United States Patent
Rabiner et al.

(10) Patent No.: US 8,672,982 B2
(45) Date of Patent: Mar. 18, 2014

(54) APPARATUS AND METHODS FOR REPAIRING CRANIOMAXILLOFACIAL BONES USING CUSTOMIZED BONE PLATES

(71) Applicant: IlluminOss Medical, Inc., East Providence, RI (US)

(72) Inventors: Robert A. Rabiner, Tiveton, RI (US); Joseph John Crisco, III, Barrington, RI (US)

(73) Assignee: Illuminoss Medical, Inc., East Providence, RI (US)

( * ) Notice: Subject to any disclaimer, the term of this patent is extended or adjusted under 35 U.S.C. 154(b) by 0 days.

(21) Appl. No.: 13/772,947

(22) Filed: Feb. 21, 2013

(65) Prior Publication Data

US 2013/0158607 A1    Jun. 20, 2013

Related U.S. Application Data

(63) Continuation of application No. 11/964,370, filed on Dec. 26, 2007, now Pat. No. 8,403,968.

(51) Int. Cl.
    *A61B 17/80*      (2006.01)

(52) U.S. Cl.
    USPC ............ 606/285; 606/280; 606/192; 606/62; 606/63; 606/71

(58) Field of Classification Search
    USPC ................ 606/92, 86 R, 93, 94, 283, 284, 70
    See application file for complete search history.

(56) References Cited

U.S. PATENT DOCUMENTS

| 4,280,233 A | 7/1981 | Raab |
| 4,294,251 A | 10/1981 | Greenwald et al. |

(Continued)

FOREIGN PATENT DOCUMENTS

| DE | 40 28 466 | 3/1992 |
| EP | 0 709 698 | 5/1996 |

(Continued)

OTHER PUBLICATIONS

Jovanovic et al., "Fixion Nails for Humeral Fractures, Injury", Int. J. Care Injured, vol. 35, Issue 11, pp. 1140-1142, Nov. 2004.

(Continued)

*Primary Examiner* — Sameh Boles
*Assistant Examiner* — Samuel Hanna
(74) *Attorney, Agent, or Firm* — Greenberg Traurig, LLP; David J. Dykeman; Roman Fayerberg

(57) ABSTRACT

Bone plates and methods of using the bone plates for adjoining bone fragments are disclosed herein. A device for adjoining at least two bone fragments includes a delivery catheter having an elongated shaft with a proximal end, a distal end, and a longitudinal axis therebetween, wherein the delivery catheter has an inner void for passage of at least one filling material and an inner lumen for passage of a light source; a conformable bone plate releasably engaging the distal end of the delivery catheter, wherein the conformable bone plate has a first surface, a second surface, a proximal end, and a distal end and at least one aperture extending from the first surface to the second surface for receiving a fastener; and an adapter releasably engaging the proximal end of the delivery catheter for receiving the light source and a delivery system housing the at least one filling material.

10 Claims, 10 Drawing Sheets

(56) References Cited

U.S. PATENT DOCUMENTS

| | | | |
|---|---|---|---|
| 4,313,434 A | 2/1982 | Segal | |
| 4,341,691 A | 7/1982 | Anuta | |
| 4,369,772 A | 1/1983 | Miller | |
| 4,414,608 A | 11/1983 | Furihata | |
| 4,422,719 A | 12/1983 | Orcutt | |
| 4,433,898 A | 2/1984 | Nasiri | |
| 4,462,394 A | 7/1984 | Jacobs | |
| 4,466,435 A | 8/1984 | Murray | |
| 4,562,598 A | 1/1986 | Kranz | |
| 4,686,973 A | 8/1987 | Frisch | |
| 4,697,584 A | 10/1987 | Haynes | |
| 4,735,625 A | 4/1988 | Davidson | |
| 4,870,953 A | 10/1989 | DonMichael et al. | |
| 4,888,024 A | 12/1989 | Powlan | |
| 4,904,391 A | 2/1990 | Freeman | |
| 4,961,424 A | 10/1990 | Kubota et al. | |
| 4,963,151 A | 10/1990 | Ducheyne et al. | |
| 4,969,888 A | 11/1990 | Scholten et al. | |
| 5,030,093 A | 7/1991 | Mitnick | |
| 5,049,157 A | 9/1991 | Mittelmeier et al. | |
| 5,085,660 A | 2/1992 | Lin | |
| 5,092,899 A | 3/1992 | Forte | |
| 5,102,413 A | 4/1992 | Poddar | |
| 5,108,404 A | 4/1992 | Scholten et al. | |
| 5,112,333 A | 5/1992 | Fixel | |
| 5,295,733 A | 3/1994 | LeBegue | |
| 5,295,962 A | 3/1994 | Crocker et al. | |
| 5,303,718 A | 4/1994 | Krajicek | |
| 5,316,550 A | 5/1994 | Forte | |
| 5,336,699 A | 8/1994 | Cooke et al. | |
| 5,372,598 A | 12/1994 | Luhr et al. | |
| 5,391,144 A | 2/1995 | Sakurai et al. | |
| 5,415,654 A | 5/1995 | Daikuzono | |
| 5,423,850 A | 6/1995 | Berger | |
| 5,432,876 A | 7/1995 | Appeldorn et al. | |
| 5,443,468 A | 8/1995 | Johnson | |
| 5,462,552 A | 10/1995 | Kiester | |
| 5,480,400 A | 1/1996 | Berger | |
| 5,538,514 A | 7/1996 | Hawkins | |
| 5,548,676 A | 8/1996 | Savage, Jr. | |
| 5,554,111 A | 9/1996 | Morrey et al. | |
| 5,556,429 A | 9/1996 | Felt | |
| 5,571,204 A | 11/1996 | Nies | |
| 5,658,310 A | 8/1997 | Berger | |
| 5,658,963 A | 8/1997 | Qian et al. | |
| 5,705,181 A | 1/1998 | Cooper et al. | |
| 5,707,374 A | 1/1998 | Schmidt | |
| 5,713,901 A | 2/1998 | Tock | |
| 5,795,353 A | 8/1998 | Felt | |
| 5,824,087 A | 10/1998 | Aspden et al. | |
| 5,827,289 A | 10/1998 | Reiley et al. | |
| 5,888,220 A | 3/1999 | Felt et al. | |
| 5,897,557 A | 4/1999 | Chin et al. | |
| 5,908,433 A | 6/1999 | Eager et al. | |
| 5,972,015 A | 10/1999 | Scribner et al. | |
| 5,980,075 A | 11/1999 | Sheaffer | |
| 5,980,253 A | 11/1999 | Oxman et al. | |
| 5,987,199 A | 11/1999 | Zarian et al. | |
| 5,989,230 A | 11/1999 | Frassica | |
| 6,008,264 A | 12/1999 | Ostler | |
| 6,019,761 A | 2/2000 | Gustilo | |
| 6,019,774 A | 2/2000 | Weiss et al. | |
| 6,033,411 A | 3/2000 | Preissman | |
| 6,039,762 A | 3/2000 | McKay | |
| 6,042,380 A | 3/2000 | De Rowe | |
| 6,048,346 A | 4/2000 | Reiley et al. | |
| 6,059,789 A | 5/2000 | Dinger et al. | |
| 6,066,154 A | 5/2000 | Reiley et al. | |
| 6,079,868 A | 6/2000 | Rydell | |
| 6,103,203 A | 8/2000 | Fischer | |
| 6,110,176 A | 8/2000 | Shapira | |
| 6,121,341 A | 9/2000 | Sawhney et al. | |
| 6,127,597 A | 10/2000 | Beyar et al. | |
| 6,140,452 A | 10/2000 | Felt et al. | |
| 6,159,236 A | 12/2000 | Biel | |
| 6,179,852 B1 | 1/2001 | Strickland et al. | |
| 6,195,477 B1 | 2/2001 | Denuto et al. | |
| 6,200,134 B1 | 3/2001 | Kovac et al. | |
| 6,217,581 B1 | 4/2001 | Tolson | |
| 6,223,085 B1 | 4/2001 | Dann et al. | |
| 6,224,630 B1 | 5/2001 | Bao et al. | |
| 6,235,043 B1 | 5/2001 | Reiley et al. | |
| 6,241,734 B1 | 6/2001 | Scribner et al. | |
| 6,248,110 B1 | 6/2001 | Reiley et al. | |
| 6,248,131 B1 | 6/2001 | Felt et al. | |
| 6,258,089 B1 | 7/2001 | Campbell et al. | |
| 6,261,289 B1 | 7/2001 | Levy | |
| 6,280,456 B1 | 8/2001 | Scribner et al. | |
| 6,282,013 B1 | 8/2001 | Ostler et al. | |
| 6,290,382 B1 | 9/2001 | Bourn et al. | |
| 6,299,597 B1 * | 10/2001 | Buscemi et al. | 604/101.03 |
| 6,306,177 B1 | 10/2001 | Felt et al. | |
| 6,319,255 B1 | 11/2001 | Grundei et al. | |
| 6,332,894 B1 | 12/2001 | Stalcup et al. | |
| 6,336,914 B1 | 1/2002 | Gillespie, III | |
| 6,336,930 B1 * | 1/2002 | Stalcup et al. | 606/284 |
| 6,358,252 B1 | 3/2002 | Shapira | |
| 6,387,098 B1 | 5/2002 | Cole et al. | |
| 6,395,007 B1 | 5/2002 | Bhatnagar et al. | |
| 6,416,531 B2 | 7/2002 | Chen | |
| 6,416,737 B1 | 7/2002 | Manolagas et al. | |
| 6,419,483 B1 | 7/2002 | Adam et al. | |
| 6,423,083 B2 | 7/2002 | Reiley et al. | |
| 6,425,923 B1 | 7/2002 | Stalcup et al. | |
| 6,440,444 B2 | 8/2002 | Boyce et al. | |
| 6,443,988 B2 | 9/2002 | Felt et al. | |
| 6,447,514 B1 | 9/2002 | Stalcup et al. | |
| 6,458,375 B1 | 10/2002 | Gertzman et al. | |
| 6,478,751 B1 | 11/2002 | Krueger et al. | |
| 6,485,512 B1 | 11/2002 | Cheng | |
| 6,494,883 B1 | 12/2002 | Ferree | |
| 6,524,251 B2 | 2/2003 | Rabiner et al. | |
| 6,524,313 B1 | 2/2003 | Fassier et al. | |
| 6,551,321 B1 | 4/2003 | Burkinshaw et al. | |
| 6,551,337 B1 | 4/2003 | Rabiner et al. | |
| 6,565,528 B1 | 5/2003 | Mueller | |
| 6,579,277 B1 | 6/2003 | Rabiner et al. | |
| 6,579,279 B1 | 6/2003 | Rabiner et al. | |
| 6,620,185 B1 | 9/2003 | Harvie et al. | |
| 6,623,505 B2 | 9/2003 | Scribner et al. | |
| 6,632,235 B2 | 10/2003 | Weikel et al. | |
| 6,648,881 B2 | 11/2003 | KenKnight et al. | |
| 6,652,547 B2 | 11/2003 | Rabiner et al. | |
| 6,652,587 B2 | 11/2003 | Felt et al. | |
| 6,660,013 B2 | 12/2003 | Rabiner et al. | |
| 6,679,873 B2 | 1/2004 | Rabiner et al. | |
| 6,695,781 B2 | 2/2004 | Rabiner et al. | |
| 6,695,782 B2 | 2/2004 | Rabiner et al. | |
| 6,696,073 B2 | 2/2004 | Boyce et al. | |
| 6,716,216 B1 | 4/2004 | Boucher et al. | |
| 6,719,773 B1 | 4/2004 | Boucher et al. | |
| 6,726,691 B2 | 4/2004 | Osorio et al. | |
| 6,730,048 B1 | 5/2004 | Hare et al. | |
| 6,733,451 B2 | 5/2004 | Rabiner et al. | |
| 6,733,513 B2 | 5/2004 | Boyle et al. | |
| 6,740,093 B2 | 5/2004 | Hochschuler et al. | |
| 6,755,862 B2 | 6/2004 | Keynan | |
| 6,783,530 B1 | 8/2004 | Levy | |
| 6,802,835 B2 | 10/2004 | Rabiner et al. | |
| 6,818,018 B1 | 11/2004 | Sawhney | |
| 6,852,095 B1 | 2/2005 | Ray | |
| 6,866,678 B2 | 3/2005 | Shenderova et al. | |
| 6,869,442 B2 | 3/2005 | Cheng | |
| 6,875,212 B2 | 4/2005 | Shaolian et al. | |
| 6,885,246 B2 | 4/2005 | Tsutsui et al. | |
| 6,887,246 B2 | 5/2005 | Bhatnagar et al. | |
| 6,887,275 B2 | 5/2005 | Carchidi et al. | |
| 6,899,713 B2 | 5/2005 | Shaolian et al. | |
| 6,899,719 B2 | 5/2005 | Reiley et al. | |
| 6,932,843 B2 | 8/2005 | Smith et al. | |
| 6,964,667 B2 | 11/2005 | Shaolian et al. | |
| 6,979,341 B2 | 12/2005 | Scribner et al. | |
| 6,981,981 B2 | 1/2006 | Reiley et al. | |
| 7,001,431 B2 | 2/2006 | Bao et al. | |

(56) References Cited

U.S. PATENT DOCUMENTS

| | | |
|---|---|---|
| 7,008,433 B2 | 3/2006 | Voellmicke et al. |
| 7,052,498 B2 | 5/2006 | Levy et al. |
| 7,077,865 B2 | 7/2006 | Bao et al. |
| 7,124,067 B2 | 10/2006 | Ascenzi |
| 7,141,061 B2 | 11/2006 | Williams et al. |
| 7,144,414 B2 | 12/2006 | Harvie et al. |
| 7,153,305 B2 | 12/2006 | Johnson et al. |
| 7,156,861 B2 | 1/2007 | Scribner et al. |
| 7,156,880 B2 | 1/2007 | Evans et al. |
| 7,169,140 B1 | 1/2007 | Kume |
| 7,215,863 B1 | 5/2007 | Arenella et al. |
| 7,241,303 B2 | 7/2007 | Reiss et al. |
| 7,258,692 B2 | 8/2007 | Thelen et al. |
| 7,261,720 B2 | 8/2007 | Stevens et al. |
| 7,320,709 B2 | 1/2008 | Felt et al. |
| 7,341,601 B2 | 3/2008 | Eisermann et al. |
| 7,360,542 B2 | 4/2008 | Nelson et al. |
| 7,407,616 B2 | 8/2008 | Melikechi et al. |
| 7,419,450 B2 | 9/2008 | Ito |
| 7,427,295 B2 | 9/2008 | Ellman et al. |
| 7,547,319 B2 | 6/2009 | Segal et al. |
| 7,628,800 B2 | 12/2009 | Sherman et al. |
| 7,632,277 B2 | 12/2009 | Woll et al. |
| 7,632,291 B2 | 12/2009 | Stephens et al. |
| 7,666,205 B2 | 2/2010 | Weikel et al. |
| 7,722,620 B2 | 5/2010 | Truckai et al. |
| 7,744,555 B2 | 6/2010 | DiMauro et al. |
| 7,766,965 B2 | 8/2010 | Bao et al. |
| 7,771,476 B2 | 8/2010 | Justis et al. |
| 7,776,075 B2 | 8/2010 | Bruneau et al. |
| 7,806,900 B2 | 10/2010 | Rabiner |
| 7,811,284 B2 | 10/2010 | Rabiner |
| 7,811,286 B2 | 10/2010 | Medoff |
| 7,811,290 B2 | 10/2010 | Rabiner |
| 7,842,040 B2 | 11/2010 | Rabiner et al. |
| 7,850,711 B1 | 12/2010 | Stone et al. |
| 7,879,041 B2 | 2/2011 | Rabiner et al. |
| 7,912,539 B2 | 3/2011 | Doty et al. |
| 7,947,015 B2 | 5/2011 | Herweck et al. |
| 8,034,071 B2 | 10/2011 | Scribner et al. |
| 8,123,807 B2 | 2/2012 | Kim et al. |
| 8,210,729 B2 | 7/2012 | O'Leary et al. |
| 8,246,628 B2 | 8/2012 | Rabiner |
| 8,328,402 B2 | 12/2012 | O'Leary et al. |
| 8,348,956 B2 | 1/2013 | Rabiner |
| 8,366,711 B2 | 2/2013 | Rabiner et al. |
| 8,403,968 B2 | 3/2013 | Rabiner et al. |
| 8,413,664 B2 | 4/2013 | Appling |
| 8,512,338 B2 | 8/2013 | Rabiner et al. |
| 2001/0011174 A1 | 8/2001 | Reiley et al. |
| 2001/0044626 A1 | 11/2001 | Reiley et al. |
| 2002/0156482 A1 | 10/2002 | Scribner et al. |
| 2002/0161373 A1 | 10/2002 | Osorio et al. |
| 2002/0198526 A1* | 12/2002 | Shaolian et al. ............ 606/61 |
| 2003/0028210 A1 | 2/2003 | Boyle et al. |
| 2003/0083642 A1 | 5/2003 | Boyd et al. |
| 2003/0105469 A1 | 6/2003 | Karmon |
| 2003/0114914 A1 | 6/2003 | Cheng |
| 2003/0156431 A1 | 8/2003 | Gozum et al. |
| 2003/0199850 A1 | 10/2003 | Chavez et al. |
| 2003/0212426 A1 | 11/2003 | Olson et al. |
| 2003/0229372 A1 | 12/2003 | Reiley et al. |
| 2004/0006341 A1 | 1/2004 | Shaolian et al. |
| 2004/0024388 A1 | 2/2004 | Altshuler |
| 2004/0034434 A1 | 2/2004 | Evans et al. |
| 2004/0059333 A1 | 3/2004 | Carl et al. |
| 2004/0059417 A1 | 3/2004 | Smith et al. |
| 2004/0092948 A1 | 5/2004 | Stevens et al. |
| 2004/0098015 A1 | 5/2004 | Weikel et al. |
| 2004/0117025 A1 | 6/2004 | Reindel |
| 2004/0133280 A1 | 7/2004 | Trieu |
| 2004/0167561 A1 | 8/2004 | Boucher et al. |
| 2004/0167625 A1 | 8/2004 | Beyar et al. |
| 2004/0225296 A1 | 11/2004 | Reiss et al. |
| 2004/0228142 A1 | 11/2004 | Takada et al. |
| 2004/0230309 A1 | 11/2004 | Di Mauro et al. |
| 2004/0247641 A1 | 12/2004 | Felt et al. |
| 2005/0010231 A1 | 1/2005 | Myers |
| 2005/0015140 A1 | 1/2005 | deBeer |
| 2005/0015148 A1 | 1/2005 | Jansen et al. |
| 2005/0043733 A1 | 2/2005 | Eisermann et al. |
| 2005/0043808 A1 | 2/2005 | Felt et al. |
| 2005/0049691 A1 | 3/2005 | Mericle et al. |
| 2005/0090901 A1 | 4/2005 | Studer |
| 2005/0119662 A1 | 6/2005 | Reiley et al. |
| 2005/0142315 A1 | 6/2005 | DeSimone et al. |
| 2005/0149022 A1 | 7/2005 | Shaolian et al. |
| 2005/0159749 A1 | 7/2005 | Levy et al. |
| 2005/0171604 A1 | 8/2005 | Michalow |
| 2005/0192671 A1 | 9/2005 | Bao et al. |
| 2005/0197711 A1 | 9/2005 | Cachia |
| 2005/0228260 A1 | 10/2005 | Burwell et al. |
| 2005/0234453 A1 | 10/2005 | Shaolian et al. |
| 2005/0251140 A1 | 11/2005 | Shaolian et al. |
| 2005/0284485 A9 | 12/2005 | Nelson et al. |
| 2006/0009550 A1 | 1/2006 | Messersmith et al. |
| 2006/0015105 A1 | 1/2006 | Warren et al. |
| 2006/0036253 A1 | 2/2006 | Leroux et al. |
| 2006/0084985 A1 | 4/2006 | Kim |
| 2006/0100547 A1 | 5/2006 | Rabiner et al. |
| 2006/0100635 A1 | 5/2006 | Reiley et al. |
| 2006/0100706 A1 | 5/2006 | Shadduck et al. |
| 2006/0111726 A1 | 5/2006 | Felt et al. |
| 2006/0122625 A1 | 6/2006 | Truckai et al. |
| 2006/0142747 A1 | 6/2006 | Appling |
| 2006/0155296 A1 | 7/2006 | Richter |
| 2006/0173464 A1 | 8/2006 | Ellman et al. |
| 2006/0183811 A1 | 8/2006 | Melikechi et al. |
| 2006/0184246 A1 | 8/2006 | Zwirkoski |
| 2006/0195165 A1 | 8/2006 | Gertner et al. |
| 2006/0217747 A1 | 9/2006 | Ferree |
| 2006/0229617 A1 | 10/2006 | Meller et al. |
| 2006/0247787 A1 | 11/2006 | Rydell et al. |
| 2006/0253102 A1 | 11/2006 | Nance et al. |
| 2006/0253200 A1 | 11/2006 | Bao et al. |
| 2006/0258981 A1 | 11/2006 | Eidenschink |
| 2006/0264950 A1 | 11/2006 | Nelson et al. |
| 2006/0264951 A1 | 11/2006 | Nelson et al. |
| 2006/0264952 A1 | 11/2006 | Nelson et al. |
| 2006/0265077 A1 | 11/2006 | Zwirkoski |
| 2006/0271061 A1 | 11/2006 | Beyar et al. |
| 2006/0276793 A1 | 12/2006 | Berry |
| 2006/0276819 A1 | 12/2006 | Osorio et al. |
| 2006/0282169 A1 | 12/2006 | Felt et al. |
| 2006/0287730 A1 | 12/2006 | Segal et al. |
| 2007/0027547 A1 | 2/2007 | Rydell et al. |
| 2007/0067032 A1 | 3/2007 | Felt et al. |
| 2007/0087031 A1 | 4/2007 | Ashman et al. |
| 2007/0118143 A1 | 5/2007 | Ralph et al. |
| 2007/0123876 A1 | 5/2007 | Czartoski et al. |
| 2007/0123877 A1 | 5/2007 | Goldin et al. |
| 2007/0123878 A1 | 5/2007 | Shaver et al. |
| 2007/0161991 A1 | 7/2007 | Altarac et al. |
| 2007/0198023 A1 | 8/2007 | Sand et al. |
| 2007/0225705 A1 | 9/2007 | Osario et al. |
| 2007/0255287 A1 | 11/2007 | Rabiner |
| 2008/0015500 A1 | 1/2008 | Herweck et al. |
| 2008/0021474 A1 | 1/2008 | Bonutti et al. |
| 2008/0039854 A1 | 2/2008 | Rabiner |
| 2008/0080205 A1 | 4/2008 | Forrester et al. |
| 2008/0103505 A1 | 5/2008 | Fransen |
| 2008/0125784 A1 | 5/2008 | Rabiner et al. |
| 2008/0154368 A1 | 6/2008 | Justis |
| 2008/0154373 A1 | 6/2008 | Protopsaltis et al. |
| 2008/0183122 A1 | 7/2008 | Fisher et al. |
| 2008/0188858 A1 | 8/2008 | Luzzi et al. |
| 2008/0234820 A1 | 9/2008 | Felt et al. |
| 2008/0249529 A1 | 10/2008 | Zarda et al. |
| 2008/0255560 A1 | 10/2008 | Myers et al. |
| 2008/0269750 A1 | 10/2008 | Justin |
| 2008/0287951 A1 | 11/2008 | Stoneburger et al. |
| 2009/0018524 A1 | 1/2009 | Greenhalgh et al. |
| 2009/0024166 A1 | 1/2009 | Carl et al. |
| 2009/0048629 A1 | 2/2009 | Rabiner |

(56) References Cited

U.S. PATENT DOCUMENTS

| | | |
|---|---|---|
| 2009/0054900 A1 | 2/2009 | Rabiner et al. |
| 2009/0093887 A1 | 4/2009 | Walter et al. |
| 2009/0112196 A1 | 4/2009 | Rabiner et al. |
| 2009/0171265 A1 | 7/2009 | Doty et al. |
| 2009/0171358 A1 | 7/2009 | Chang et al. |
| 2009/0177204 A1 | 7/2009 | Colleran et al. |
| 2009/0182336 A1 | 7/2009 | Brenzel et al. |
| 2009/0187192 A1 | 7/2009 | Rabiner et al. |
| 2009/0216232 A1 | 8/2009 | Buford, III et al. |
| 2009/0228007 A1 | 9/2009 | Justin et al. |
| 2009/0254064 A1 | 10/2009 | Boatman |
| 2009/0287309 A1 | 11/2009 | Walch et al. |
| 2010/0234958 A1 | 9/2010 | Linares |
| 2010/0241178 A1 | 9/2010 | Tilson et al. |
| 2010/0249942 A1 | 9/2010 | Goswami et al. |
| 2010/0256641 A1 | 10/2010 | Rabiner et al. |
| 2010/0262069 A1 | 10/2010 | Rabiner et al. |
| 2010/0262188 A1 | 10/2010 | Rabiner et al. |
| 2010/0265733 A1 | 10/2010 | O'Leary et al. |
| 2010/0318087 A1 | 12/2010 | Scribner et al. |
| 2010/0331850 A1 | 12/2010 | Rabiner |
| 2011/0004213 A1 | 1/2011 | Rabiner et al. |
| 2011/0009871 A1 | 1/2011 | Rabiner |
| 2011/0029093 A1 | 2/2011 | Bojarski et al. |
| 2011/0046746 A1 | 2/2011 | Rabiner et al. |
| 2011/0098713 A1 | 4/2011 | Rabiner et al. |
| 2011/0110114 A1 | 5/2011 | Papac et al. |
| 2011/0118740 A1 | 5/2011 | Rabiner et al. |
| 2011/0160870 A1 | 6/2011 | Baumgartner et al. |
| 2011/0166306 A1 | 7/2011 | Stansbury et al. |
| 2011/0313356 A1 | 12/2011 | Rabiner et al. |
| 2012/0165941 A1 | 6/2012 | Rabiner et al. |
| 2012/0262939 A1 | 10/2012 | O'Leary et al. |
| 2012/0289968 A1 | 11/2012 | Rabiner |
| 2013/0003406 A1 | 1/2013 | O'Leary et al. |
| 2013/0006304 A1 | 1/2013 | Rabiner et al. |
| 2013/0013008 A1 | 1/2013 | Rabiner et al. |
| 2013/0013009 A1 | 1/2013 | Colleran et al. |
| 2013/0013010 A1 | 1/2013 | Rabiner et al. |
| 2013/0023876 A1 | 1/2013 | Rabiner et al. |
| 2013/0023877 A1 | 1/2013 | Rabiner et al. |
| 2013/0023886 A1 | 1/2013 | Rabiner et al. |
| 2013/0041472 A1 | 2/2013 | Rabiner et al. |
| 2013/0046390 A1 | 2/2013 | Rabiner et al. |
| 2013/0066326 A1 | 3/2013 | Rabiner et al. |
| 2013/0184715 A1 | 7/2013 | Rabiner et al. |

FOREIGN PATENT DOCUMENTS

| | | |
|---|---|---|
| JP | 2001-527437 | 12/2001 |
| JP | 2004-526525 | 9/2002 |
| JP | 2005-511143 | 4/2005 |
| JP | 2006-212425 | 8/2006 |
| NL | 9001858 | 3/1992 |
| WO | WO 98/38918 | 9/1998 |
| WO | WO 02/43628 | 6/2002 |
| WO | WO 03/47472 | 6/2003 |
| WO | WO 2004/045393 | 6/2004 |
| WO | WO 2004/058045 | 7/2004 |
| WO | WO 2004/073563 | 9/2004 |
| WO | WO 2004/112661 | 12/2004 |
| WO | WO 2005/112804 | 12/2005 |
| WO | WO 2006/016807 | 2/2006 |
| WO | WO 2008/039811 | 4/2007 |
| WO | WO 2007/059259 | 5/2007 |
| WO | WO 2007/127255 | 11/2007 |
| WO | WO 2007/127260 | 11/2007 |
| WO | WO 2008/063265 | 5/2008 |
| WO | WO 2009/059090 | 5/2009 |
| WO | WO 2009/082688 | 7/2009 |
| WO | WO 2009/131999 | 10/2009 |
| WO | WO 2010/050965 | 5/2010 |
| WO | WO 2010/118158 | 10/2010 |
| WO | WO 2011/060062 | 5/2011 |
| WO | WO 2011/071567 | 6/2011 |
| WO | WO 2011/162910 | 12/2011 |
| WO | WO 2012/088432 | 6/2012 |
| WO | WO 2013/013069 | 1/2013 |
| WO | WO 2013/013071 | 1/2013 |
| WO | WO 2013/013072 | 1/2013 |
| WO | WO 2013/059609 | 4/2013 |

OTHER PUBLICATIONS

Maruyama et al., "Metacarpal Fracture Fixation with Absorbable Polyglycolide Rods and Stainless Steel K Wires: A Biomechanical Comparison", Journal of Biomedical Materials Research (Applied Biomaterials), vol. 33, Issue 1, pp. 9-12, Apr. 1996.

Waris et al., "Bioabsorbable Miniplating Versus Metallic Fixation for Metacarpal Fractures", Clinical Orthopaedics and Related Research, No. 410, pp. 310-319, May 2003.

Waris et al., "Self-Reinforced Bioabsorbable Versus Metallic Fixation Systems for Metacarpal and Phalangeal Fractures: A Biomechanical Study", The Journal of Hand Surgery, vol. 27A, No. 5, pp. 902-909, Sep. 2002.

PCT International Search Report based on PCT/US07/20402 dated Apr. 1, 2008.

PCT International Search Report based on PCT/US07/10050 dated Apr. 17, 2008.

PCT International Search Report based on PCT/US07/10038 dated Aug. 27, 2008.

PCT International Search Report based on PCT/US08/81929 dated Jan. 12, 2009.

PCT International Search Report based on PCT/US08/81924 dated Feb. 9, 2009.

PCT International Search Report based on PCT/US08/87630 dated Feb. 24, 2009.

PCT International Search Report based on PCT/US10/30275 dated Aug. 11, 2010.

PCT International Search Report based on PCT/US10/56219 dated Jan. 20, 2011.

PCT International Search Report based on PCT/US10/46003 dated May 24, 2011.

PCT International Search Report based on PCT/US11/38389 dated Sep. 22, 2011.

PCT International Search Report based on PCT/US11/66871 dated May 1, 2012.

USPTO Office Action in U.S. Appl. No. 11/789,906 mailed Apr. 29, 2009.

USPTO Office Action in U.S. Appl. No. 11/789,906 mailed Mar. 11, 2010.

USPTO Office Action in U.S. Appl. No. 11/789,906 mailed Apr. 30, 2010.

USPTO Office Action in U.S. Appl. No. 11/789,907 mailed May 11, 2010.

USPTO Office Action in U.S. Appl. No. 11/903,123 mailed Jul. 1, 2010.

USPTO Office Action in U.S. Appl. No. 11/964,370 mailed Dec. 9, 2010.

USPTO Office Action in U.S. Appl. No. 11/964,370 mailed Apr. 28, 2011.

USPTO Office Action in U.S. Appl. No. 11/964,370 mailed Sep. 23, 2011.

USPTO Office Action in U.S. Appl. No. 11/964,370 mailed Mar. 16, 2012.

USPTO Office Action in U.S. Appl. No. 12/262,411 mailed Sep. 1, 2010.

USPTO Office Action in U.S. Appl. No. 12/755,784 mailed Dec. 23, 2011.

USPTO Office Action in U.S. Appl. No. 12/756,014 mailed May 11, 2012.

USPTO Office Action in U.S. Appl. No. 12/858,924 mailed Oct. 24, 2011.

USPTO Office Action in U.S. Appl. No. 12/858,924 mailed Apr. 4, 2012.

USPTO Office Action in U.S. Appl. No. 12/875,460 mailed Mar. 8, 2012.

(56) References Cited

OTHER PUBLICATIONS

USPTO Office Action in U.S. Appl. No. 12/886,288 mailed Dec. 27, 2011.
USPTO Office Action in U.S. Appl. No. 12/262,370 mailed May 29, 2012.
USPTO Office Action in U.S. Appl. No. 12/943,544 mailed Jun. 8, 2012.
USPTO Office Action in U.S. Appl. No. 12/886,288 mailed Jun. 26, 2012.
USPTO Office Action in U.S. Appl. No. 11/964,370 mailed Jul. 6, 2012.
Extended European Search Report based on EP 07 75 6022 dated Jul. 30, 2012.
Extended European Search Report based on EP 07 75 6016 dated Jul. 30, 2012.
USPTO Office Action in U.S. Appl. No. 12/755,784 mailed Aug. 1, 2012.
USPTO Office Action in U.S. Appl. No. 12/858,924 mailed Aug. 2, 2012.
USPTO Office Action in U.S. Appl. No. 12/886,288 mailed Aug. 15, 2012.
PCT International Search Report based on PCT/US12/47447 dated Oct. 2, 2012.
PCT International Search Report based on PCT/US12/47446 dated Oct. 15, 2012.
PCT International Search Report based on PCT/US12/47444 dated Oct. 18, 2012.
USPTO Office Action in U.S. Appl. No. 12/756,014 mailed Oct. 25, 2012.
USPTO Office Action in U.S. Appl. No. 12/859,680 mailed Nov. 9, 2012.
USPTO Office Action in U.S. Appl. No. 12/943,544 mailed Dec. 3, 2012.
USPTO Office Action in U.S. Appl. No. 12/859,680 mailed Jan. 17, 2013.
USPTO Office Action in U.S. Appl. No. 12/262,370 mailed Dec. 14, 2012.
International Search Report and Written Opinion for PCT/US2012/061047 mailed Jan. 7, 2013.
USPTO Office Action in U.S. Appl. No. 12/756,014 mailed Jan. 22, 2013.
USPTO Office Action in U.S. Appl. No. 13/088,916 mailed Jan. 23, 2013.
Supplemental European Search Report based on EP 08 87 7881 dated May 15, 2013.
USPTO Office Action in U.S. Appl. No. 13/617,557 mailed Feb. 4, 2013.
USPTO Office Action in U.S. Appl. No. 12/755,784 mailed Mar. 13, 2013.
USPTO Office Action in U.S. Appl. No. 13/616,416 mailed Mar. 25, 2013.
USPTO Office Action in U.S. Appl. No. 13/561,249 mailed Apr. 23, 2013.
USPTO Office Action in U.S. Appl. No. 12/262,370 mailed Apr. 26, 2013.
USPTO Office Action in U.S. Appl. No. 13/088,916 mailed May 13, 2013.
USPTO Office Action in U.S. Appl. No. 12/859,680 mailed Jul. 9, 2013.
USPTO Office Action in U.S. Appl. No. 13/561,249 mailed Sep. 16, 2013.
USPTO Office Action in U.S. Appl. No. 13/088,916 mailed Sep. 17, 2013.
USPTO Office Action in U.S. Appl. No. 12/943,544 mailed Sep. 25, 2013.
USPTO Office Action in U.S. Appl. No. 13/617,557 mailed Oct. 9, 2013.

* cited by examiner

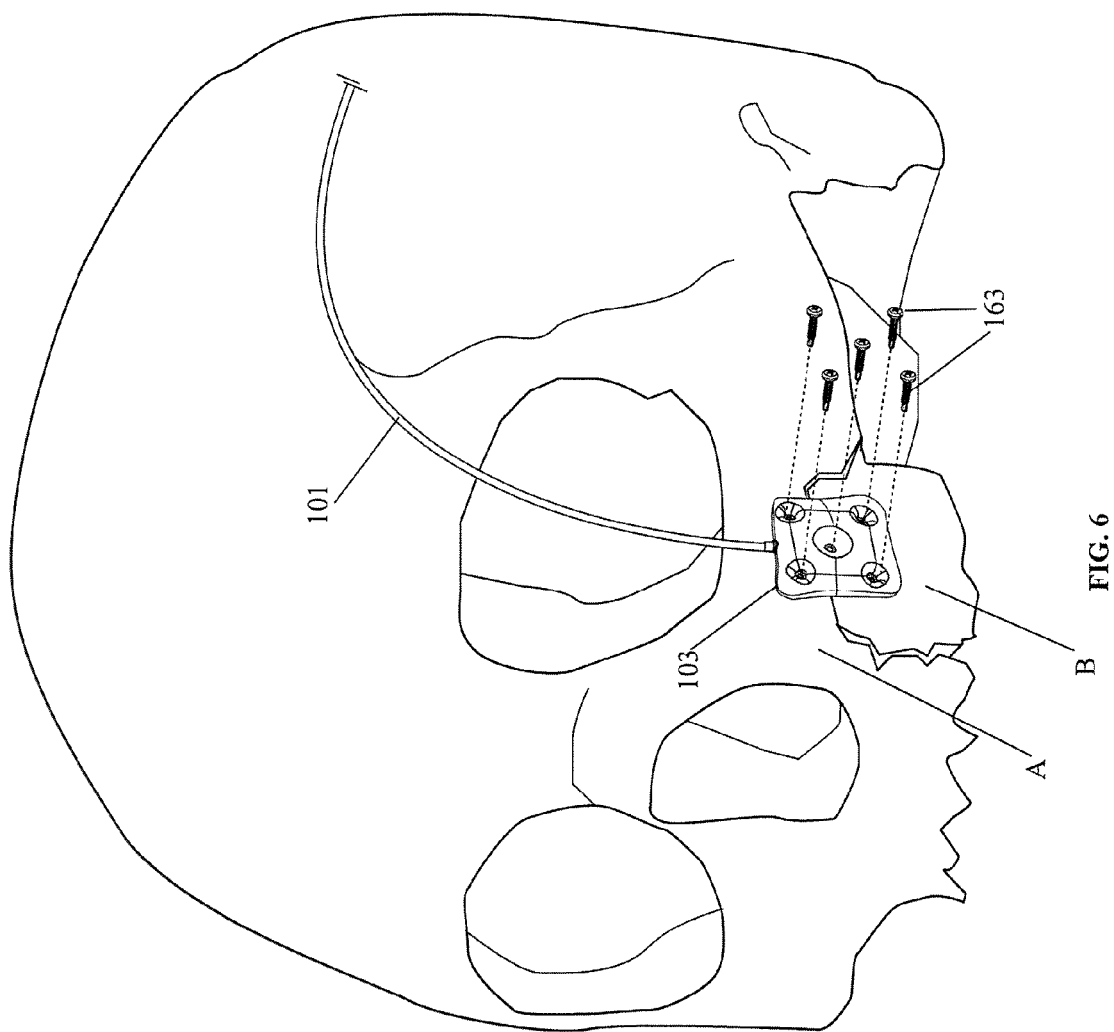

APPARATUS AND METHODS FOR REPAIRING CRANIOMAXILLOFACIAL BONES USING CUSTOMIZED BONE PLATES

RELATED APPLICATIONS

This application is a continuation of U.S. application Ser. No. 11/964,370, filed on Dec. 26, 2007, which is incorporated herein by reference in its entirety.

FIELD

The embodiments disclosed herein relate to medical devices for use in adjoining bone fragments, and more particularly to conformable bone plates for repair of craniomaxillofacial bony defects and methods of using conformable bone plates.

BACKGROUND

Maxillofacial and craniofacial injuries encompass any injury to the mouth, face and jaw. Common serious injury to the face occurs when bones are broken (a fracture). Fractures can involve the lower jaw, upper jaw, palate, cheekbones, eye sockets and combinations of these bones. The fracture needs to be held in the correct position while the bone is healing. In most cases this requires fixing the bones using metal or biodegradable plates and screws, known as internal fixation.

There are a variety of micro, mini and reconstruction plating systems. One of the most commonly used plating system developed to date is the Luhr system manufactured by Howmedica, Inc. Subsequently, based on the original concept by Luhr, several complete systems have been developed for use in all the various situations encountered in trauma and reconstructive surgery of the facial skeleton. Techniques and materials used for the internal fixation of the maxillofacial skeleton continue to evolve and improve. For example, metal plates have been used for the repair of craniomaxillofacial bone fractures. These metal plates are generally secured to the fractured bone portions with fasteners such as screws. The plates conventionally employed generally comprise small, generally flat, elongated sections of metal. The sections contain round screw holes at various points along their lengths for fastening the sections to bone. The metal plate is then bent into shape and secured to the fractured bone using a plurality of fasteners seated within the screw holes. While known systems utilizing plates and fasteners for aiding the osteosynthesis of severed bone regions have proven to be acceptable for certain applications, such systems are nevertheless susceptible to improvements that may enhance their performance. For example, metals are difficult to shape and are hampered by disadvantages such as infection and corrosion. Several resorbable plate and screw fixation systems are now available for use in the maxillofacial skeleton. These systems allow initial stable fixation of bone segments during the bone-healing phase and then gradually are reabsorbed through physiologic processes.

Regardless of the plate system used, the plate must be contoured to lay passively against the underlying bone surfaces. Therefore, even though the plating systems themselves are manufactured with extremely precise tolerances, an element of imprecision remains for surgeons who repair facial fractures and do orthognathic surgery or reconstructive procedures repositioning the facial skeletal structures to improve esthetics or function. When an osteotomy, fracture, or bone graft is placed into appropriate position, the bone plate has to be manually bent to the contour of the anatomy. This manual manipulation creates a substantial element of imprecision even with the use of templates. Maladapted bone plates lead to inappropriate bone contour, irritation of the overlying soft tissues, abnormal anatomy or contour defects and either nonunion, malunion or unaesthetic results.

Thus, there is a need in the art for devices and methods for repairing maxillofacial and craniofacial bony defects that are easy to use, biocompatible, require minimal manipulation once in place, and are customizable on a patient-by-patient basis.

SUMMARY

Conformable bone plates and methods for using the bone plates to adjoin bone fragments are disclosed herein. According to aspects illustrated herein, there is provided a bone plate for adjoining at least two bone fragments that includes a flexible pad capable of expanding, the pad having a first surface and a second surface; and at least one aperture for receiving a fastener, the at least one aperture extending from the first surface to the second surface, wherein the bone plate is able to move from a first compact position to a second expanded position and is contoured to passively engage against the at least two bone fragments.

According to aspects illustrated herein, there is provided a device for adjoining at least two bone fragments that includes a delivery catheter having an elongated shaft with a proximal end, a distal end, and a longitudinal axis therebetween, wherein the delivery catheter has an inner void for passage of at least one filling material and an inner lumen for passage of light from a light source; a conformable bone plate releasably engaging the distal end of the delivery catheter, wherein the conformable bone plate has a first surface, a second surface, a proximal end, and a distal end and at least one aperture extending from the first surface to the second surface for receiving a fastener; and an adapter releasably engaging the proximal end of the delivery catheter for receiving light from the light source and a delivery system housing the at least one filling material.

According to aspects illustrated herein, there is provided a method for adjoining at least two bone fragments that includes providing a device for adjoining at least two bone fragments, the device including a conformable bone plate engaged to a delivery catheter having an elongated shaft with a proximal end, a distal end, and a longitudinal axis therebetween, wherein the conformable bone plate has at least one aperture extending from a first surface of the bone plate to a second surface of the bone plate for receiving a fastener to affix the bone plate to the at least two bone fragments; positioning the conformable bone plate over an exterior surface spanning the at least two bone fragments; attaching a delivery system housing at least one filling material to the delivery catheter, wherein the elongated shaft of the delivery catheter has an inner void for passage of the at least one filling material to the conformable bone plate; inserting a light source into the delivery catheter, wherein the elongated shaft of the delivery catheter has an inner lumen for passage of the light source to the conformable bone plate; infusing the at least one filling material through the elongated shaft of the delivery catheter and into the conformable bone plate to expand the conformable bone plate; activating the light source to harden the at least one filling material in the expanded conformable bone plate; releasing the hardened conformable bone plate from the delivery catheter; and affixing the conformable bone plate to the exterior surfaces of the at least two bone fragments to adjoin the bone fragments.

BRIEF DESCRIPTION OF THE DRAWINGS

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

FIG. 1A shows a conformable bone plate of the device in a deflated state. FIG. 1B shows a conformable bone plate of the device in an inflated state.

FIG. 3A shows a perspective view of a distal end of the device. FIG. 3B shows a side cross-sectional view taken along line A-A in FIG. 3A of the device. FIG. 3C shows a cross-sectional view of the device taken along line B-B in FIG. 3A.

FIG. 5A shows a side cross-sectional view of the device taken along line A-A from FIG. 3A. FIG. 5B shows a cross-sectional view of the device taken along line B-B from FIG. 3A.

FIG. 6 shows the placement of a conformable bone plate of the presently disclosed embodiments during repair of a craniomaxillofacial injury.

While the above-identified drawings set forth presently disclosed embodiments, other embodiments are also contemplated, as noted in the discussion. This disclosure presents illustrative embodiments by way of representation and not limitation. Numerous other modifications and embodiments may be devised by those skilled in the art which fall within the scope and spirit of the principles of the presently disclosed embodiments.

DETAILED DESCRIPTION

Medical devices and methods for repairing maxillofacial and craniofacial injuries are disclosed herein. The craniomaxillofacial bone plates of the presently disclosed embodiments are made from a pliable, resilient, conformable, biocompatible, and strong material. At least one filling material is contained within the bone plates of the presently disclosed embodiments. During a procedure for repairing a craniomaxillofacial injury, a conformable bone plate is brought to the site of injury (an osteotomy, a fracture, a bone graft or other site of injury) in a deflated state. Once in place, the bone plate is expanded from a deflated state to an inflated state in situ by the addition of the at least one filling material. The addition of the at least one filling material may be precisely controlled such that the bone plate will resemble the contour of the site, on a patient-by-patient basis. Once the desired level of expansion is achieved, the at least one filling material is hardened within the bone plate using a light source. The hardened bone plate is then affixed to the site using fasteners. The customizable bone plate of the presently disclosed embodiments provides support and proper orientation of the bony defect resulting in the repair, healing, and strengthening of the defect.

Filling materials include, but are not limited to, bone reinforcing mixtures (such as bone cement mixtures, bone void fillers, epoxies, glues and similar adhesives), orthopedic wires, stainless-steel rods, metal pins, and other similar devices. The filling material may be a natural or synthetic material for strengthening, replacing, or reinforcing of bones or bone tissue. Bone reinforcing mixtures include glues, epoxies, adhesives, cements, hard tissue replacement polymers, biodegradable polymers such as PLA, PGA, and PLA-PGA copolymers, natural coral, hydroxyapatite, beta-tricalcium phosphate, and various other biomaterials known in the art for strengthening, replacing or reinforcing bones. As inert materials, bone reinforcing mixtures may be incorporated into surrounding tissue or gradually replaced by original tissue. Those skilled in the art will recognize that numerous bone reinforcing mixtures known in the art are within the spirit and scope of the presently disclosed embodiments.

A device disclosed herein may be used for the repair of a craniomaxillofacial bony defect related to trauma, tumors, as well as for developmental and congenital craniomaxillofacial deformities.

Figure 1A:
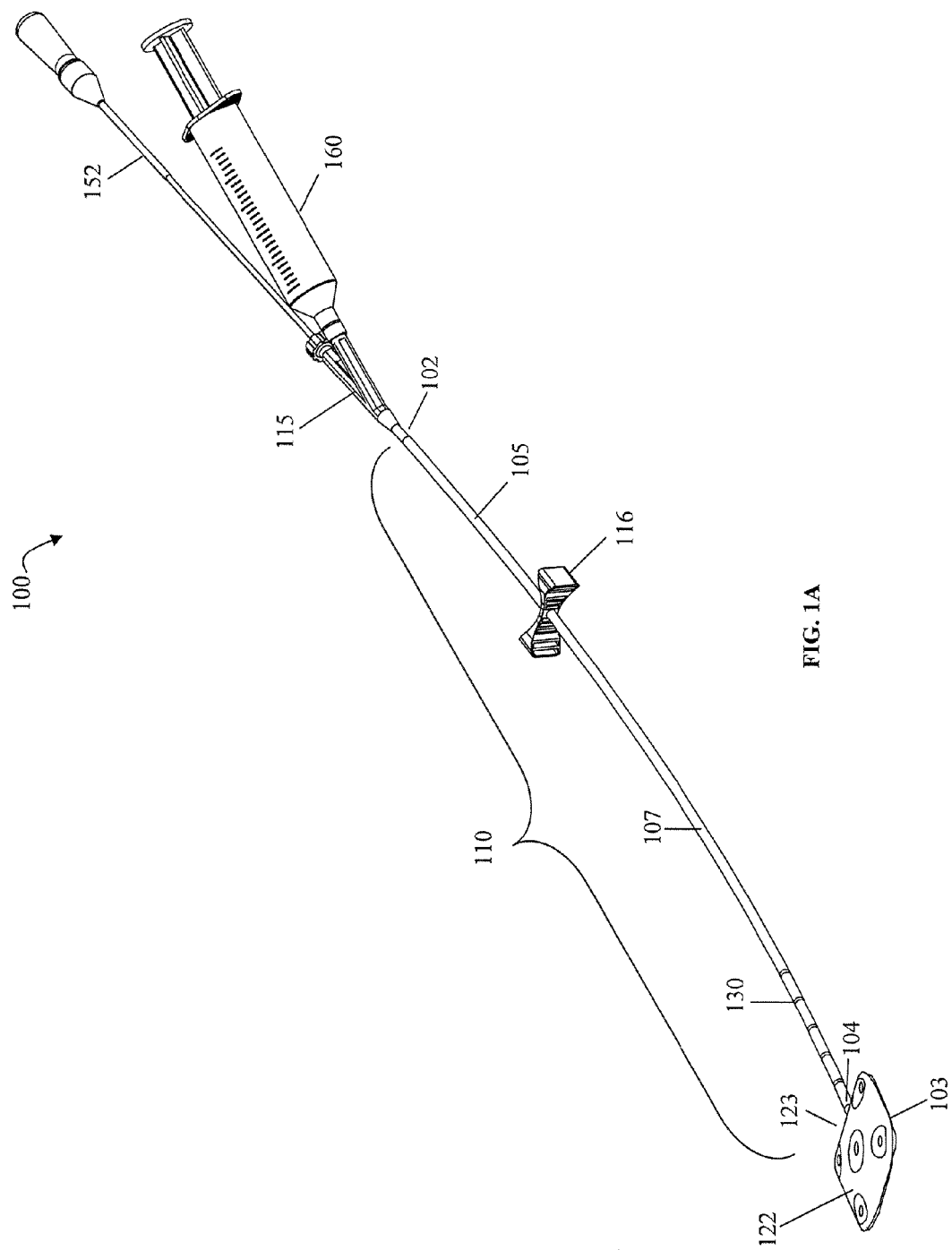
FIG. 1A and FIG. 1B show perspective views of a device for repairing a craniomaxillofacial injury of the presently disclosed embodiments.
Figure 1B:
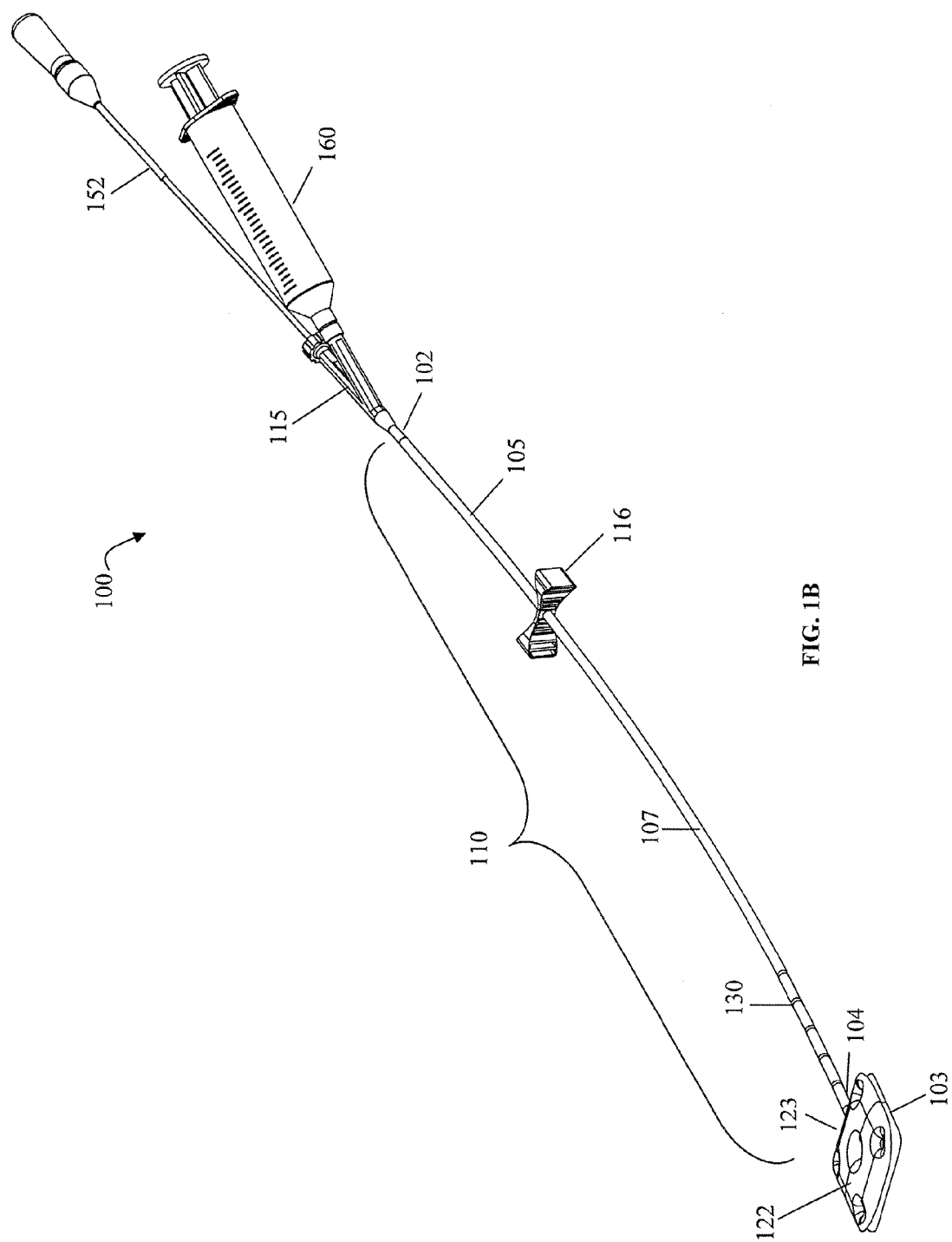
Figure 2:
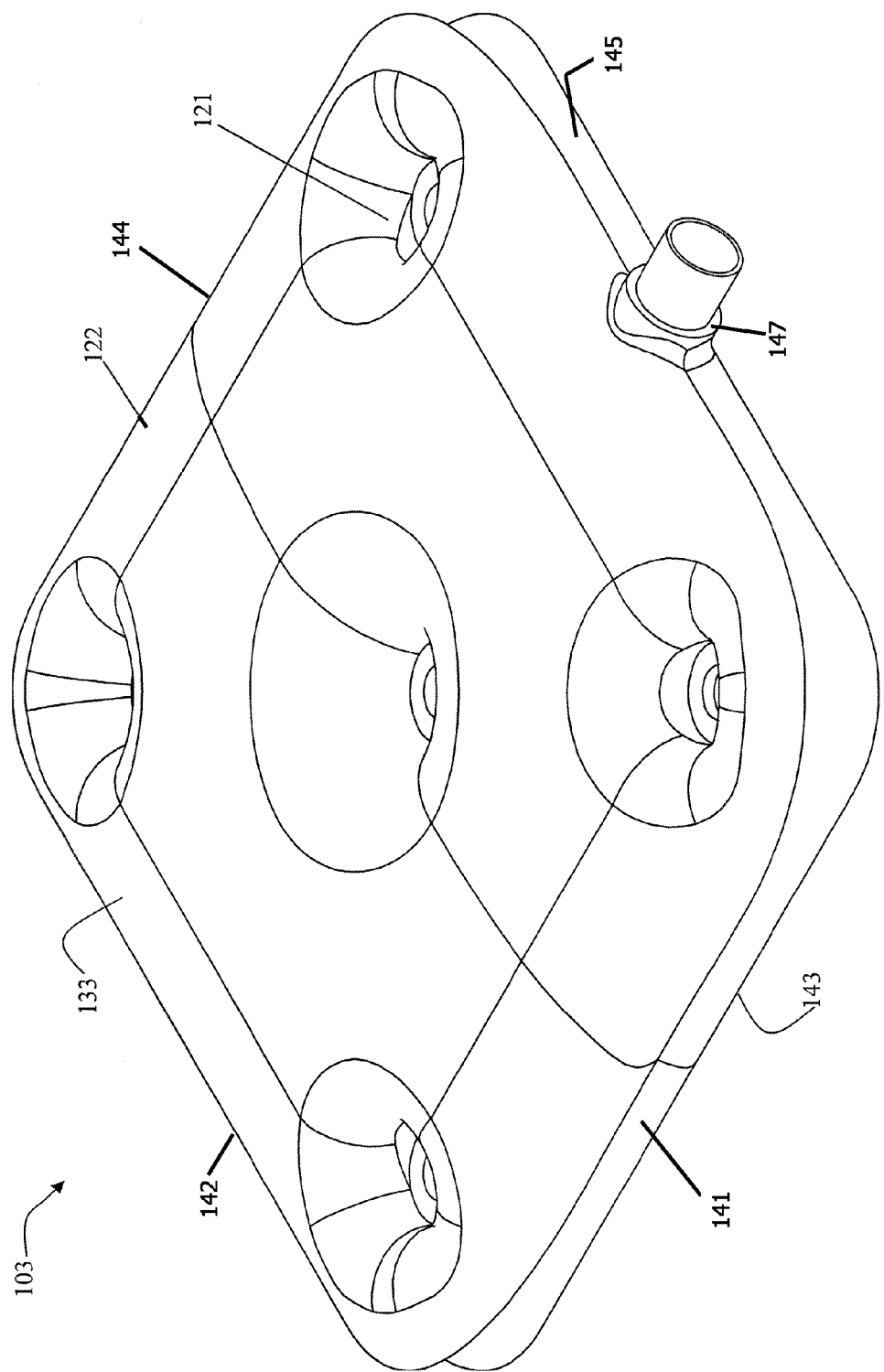
FIG. 2 shows an enlarged perspective view of the conformable bone plate of the device in an inflated state.

The main components of a device for repairing a craniomaxillofacial bony defect are shown generally in FIG. 1A and FIG. 1B in conjunction with FIG. 2. The device 100 includes a delivery catheter 110 having an elongated shaft with a proximal end 102, a distal end 104, and a longitudinal axis therebetween. In an embodiment, the delivery catheter 110 has a diameter of about 3 mm. The distal end 104 of the delivery catheter 110 terminates in a releasable conformable bone plate 103. The bone plate 103 may move from a deflated state (FIG. 1A) to an inflated state (FIG. 1B) when at least one filling material is delivered to the bone plate 103. In an embodiment, the thickness of the deflated conformable bone plate 103 is about 7 mm. An inflated conformable bone plate 103, as shown in FIG. 1B, may have a size of about 3 mm by about 10 mm. Alternately, the inflated conformable bone plate 103 may have a size of about 25 mm by about 25 mm. Those skilled in the art will recognize that variations within these ranges are possible and still within the scope and spirit of the presently disclosed embodiments. The filling material is delivered to the bone plate 103 via an inner void capable of allowing the filling material to pass through. In an embodiment, the filling material is a UV-activated glue.

A stiffening member 105 may surround the elongated shaft of the delivery catheter 110 and provides rigidity over the elongated shaft. A pusher or stabilizer 116 is loaded proximal to the bone plate 103. A slip sleeve 107 may surround the stiffening member 105. In an embodiment, the slip sleeve 107 surrounds the stiffening member 105 from a proximal end 123 of the bone plate 103 up until the pusher 116. One or more radiopaque markers or bands 130 may be placed at various locations along the bone plate 103 and/or the slip sleeve 107 for alignment of the device 100 during fluoroscopy or other forms of visualization. The one or more radiopaque bands 130, using radiopaque materials such as barium sulfate, tantalum, or other materials known to increase radiopacity, allows a medical professional to view the device 100 using fluoroscopy techniques. The one or more radiopaque bands 130 also provide visibility during inflation of the bone plate 103 to determine the precise positioning of the bone plate 103 and the device 100 during placement and inflation. The one or more radiopaque bands 130 permit visualization of any voids that may be created by air that gets entrapped in the bone plate 103. The one or more radiopaque bands 130 permit visualization to preclude the bone plate 103 from misengaging or not meeting the bony defects due to improper inflation. It may be desirable to imbed radiopaque beads on the corners of the conformable bone plate 103 to assist in the visualization/location of the bone plate 103.

In an embodiment, an adapter 115, such as a Tuohy-Borst adapter, engages the proximal end 102 of the delivery catheter 110. A light source that includes a light pipe 152 may be introduced into one of the side-arms of the adapter 115 and passes within an inner lumen of the delivery catheter 110 up until the distal end 104 of the delivery catheter 110. A delivery system 160 housing the filling material may be introduced into another side-arm of the adapter 115, as shown in FIG. 1A. Alternately, a Luer fitting may engage the proximal end 102 of the delivery catheter 110 and a Luer fitting would exist on the light source such that the delivery catheter 110 and the light source would lock together.

Examples of delivery systems include, but are not limited to, caulking gun type systems, syringe systems, bag systems that contain the filling material where the delivery of the filling material is controlled using a tube clamp or any other restrictor valve. In the embodiments shown in FIG. 1A and FIG. 1B, the delivery system 160 is a syringe. In an embodiment, the syringe 160 has a control mechanism that regulates the flow of the filling material. The control mechanism of the syringe 160 allows the filling material to flow into the delivery catheter 110 and the flow may be stopped if desired. The syringe 160 makes direct contact to control the directional flow of the filling material, and the direction of flow of the filling material instantaneously changes within the delivery catheter 110 in response to a change in the direction of the syringe 160.

In an embodiment, the syringe 160 is opaque and does not allow light to penetrate within the syringe 160. Having an opaque syringe 160 ensures that the filling material contained in the syringe 160 is not exposed to light and will not cure in the syringe 160. The filling material is of a liquid consistency, as measured in Centipoise (cP), the unit of dynamic viscosity, so the filling material may be infused from the syringe 160 into the delivery catheter 110 and into the bone plate 103. Because the filling material has a liquid consistency and is viscous, the filling material may be delivered using low pressure delivery and high pressure delivery is not required, but may be used.

In an embodiment, a separation area is located at the junction between the proximal end 123 of the bone plate 103 and the delivery catheter 110. The separation area may also include an illumination band. When activated, the illumination band causes light to cure the filling material located in the bone plate 103 within the illumination band. The illumination band extends around the delivery catheter 110 and has a stress concentrator. The stress concentrator may be a notch, groove, channel or similar structure that concentrates stress in the illumination band. The stress concentrator of the illumination band may be notched, scored, indented, pre-weakened or pre-stressed to direct separation of the bone plate 103 from the elongated shaft of the delivery catheter 110 under specific torsional load. The separation area ensures that there are no leaks of filling material from the elongated shaft of the delivery catheter 110 and/or the bone plate 103. The separation area seals the bone plate 103 and removes the elongated shaft of the delivery catheter 110 by making a break at a known or predetermined site (e.g., a separation area). The separation area may be various lengths and up to about an inch long. When torque (twisting) is applied to the delivery catheter 110, the elongated shaft separates from the bone plate 103. The twisting creates a sufficient shear to break the residual filling material and create a clean separation of the plate/shaft interface. The illumination band may be connected to the light source and may be activated by a separate switch. Having a distinct switch to activate the illumination band may help to prevent inadvertent delivery of light from the light source to cure the filling material. The activation of the illumination band seals the bone plate 103 and seals the end of the delivery catheter 110, and ensures that there is a "hard seal" of the filling material at the illumination band allowing no filling material to leak from the bone plate 103 or the delivery catheter 110.

FIG. 2 shows a close-up view of the bone plate 103. The bone plate 103 is a pad having, a first surface 133, a second surface 143, a right side surface 145, a left side surface 142, a front surface 141, a back surface 144, and an inner space therebetween. The first surface 133 and the second surface 143 each have a first area. The left side surface 142 and the right side surface 145 each have a second area. The front surface 141 and the back surface 144 each have a third area. The first area is greater than the second area. A major longitudinal axis runs from the left side surface 142 to the right side surface 145, and a minor longitudinal axis runs from the first surface 133 to the second surface 143. The pad includes an opening 147 positioned only through the right side surface 145 of the pad, wherein the opening 147 is sufficiently designed to engage the delivery catheter 110. At least one pre-punched aperture 121 extends from the first surface 133 to the second surface 143, along the minor longitudinal axis, for attaching the bone plate 103 to an exterior surface of the bone fragments. In the embodiment depicted in FIG. 2, there are five pre-punched apertures 121 for attaching the bone plate 103 to the bone fragments, one aperture at each corner and one aperture in the middle. This arrangement of apertures 121 permits multiple connections to bones and ensures contouring and consistent engagement to bones. Those skilled in the art will recognize that the number and placement of the pre-punched apertures 121 on the bone plate 103 may vary and still be within the scope and spirit of the presently disclosed embodiments. The apertures 121 may be threaded or simply formed as non-threaded through holes. The apertures 121 are adapted to receive a fastener for interconnecting the bone plate 103 with a severed bone region. In an embodiment, the bone plate 103 may have a baffle structure which reduces wave motion of the filling material in the bone plate 103. Baffles would float within the bone plate 103 and may have serpentine, cone, coil or cylindrical shapes.

In an embodiment, the bone plate 103 may have a pre-defined shape to fit over a specific bony defect site. The bone plate 103 may be a pad that is round, flat, cylindrical, oval, rectangular or another shape, as long as the bone plate 103 bridges and supports fragments of fractured bone. For example, as depicted in the embodiment of FIG. 2, the pre-defined shape of the bone plate 103 is a generally square pad.

The bone plate 103 may be formed of a pliable, resilient, conformable, biocompatible, and strong material, including but not limited to urethane, polyethylene terephthalate (PET), nylon elastomer and other similar polymers. In an embodiment, the bone plate 103 is constructed out of a PET nylon aramet or other non-consumable materials. PET is a thermoplastic polymer resin of the polyester family that is used in synthetic fibers. Depending on its processing and thermal history, PET may exist both as an amorphous and as a semi-crystalline material. Semi-crystalline PET has good strength, ductility, stiffness and hardness. Amorphous PET has better ductility, but less stiffness and hardness. PET can be semi-rigid to rigid, depending on its thickness, and is very lightweight. PET is strong and impact-resistant, naturally colorless and transparent and has good resistance to mineral oils, solvents and acids.

The bone plate 103 has an outer surface 122. The outer surface 122 is resilient and puncture resistant. In an embodiment, the outer surface 122 of the bone plate 103 is substantially even and smooth. In an embodiment, the outer surface 122 of the bone plate 103 is not entirely smooth and may have some small bumps or convexity/concavity along the length. In an embodiment, the outer surface 122 of the bone plate 103 may have ribs, ridges, bumps or other shapes to help the bone plate 103 conform to the shape of a bony defect. In an embodiment, the bone plate 103 has a textured surface which provides one or more ridges that allow grabbing all portions of bony defects. In an embodiment, sand blasted surfacing on the outer surface 122 of the bone plate 103 improves the connection and adhesion between the outer surface 122 of the bone plate 103 and the bony defect. The surfacing significantly increases the amount of surface area that comes in contact with the bone resulting in a stronger grip.

The outer surface 122 of the bone plate 103 may be coated with materials such as drugs, bone glue, proteins, growth factors, or other coatings. For example, after a surgical procedure an infection may develop in a patient, requiring the patient to undergo antibiotic treatment. An antibiotic drug may be added to the outer surface 122 of the bone plate 103 to prevent or combat a possible infection. Proteins, such as, for example, the bone morphogenic protein or other growth factors have been shown to induce the formation of cartilage and bone. A growth factor may be added to the outer surface 122 of the bone plate 103 to help induce the formation of new bone. Due to the lack of thermal egress of the filling material in the bone plate 103, the effectiveness and stability of the coating is maintained. In an embodiment, a water soluble glue is applied to the outer surface 122 of the bone plate 103. When the bone plate 103 is expanded and engages a moist bone, the water soluble glue on the outer surface 122 of the bone plate 103 becomes sticky or tacky and acts as a gripping member to increase the conformal bond of the bone plate 103 to the bone. Once the bone plate 103 is inflated, the outer surface 122 of the bone plate 103 grips the bone forming a mechanical bond as well as a chemical bond. These bonds prevent the potential for a bone slippage. The water soluble glue may be cured by any light (e.g., UV not required).

The bone plate 103 of the device 100 typically does not have any valves. One benefit of having no valves is that the bone plate 103 may be inflated or deflated as much as necessary to resemble the contour of the new anatomy of an osteotomy, fracture or bone graft site. Another benefit of the bone plate 103 having no valves is the efficacy and safety of the device 100. Since there is no communication passage of filling material to the body there cannot be any leakage of material because all the material is contained within the bone plate 103. In an embodiment, a permanent seal is created between the bone plate 103 that is both hardened and affixed prior to the delivery catheter 110 being removed. In an embodiment, a permanent seal is created between the bone plate 103 that is hardened, the deliver catheter 119 is removed, and the bone plate 103 is affixed to the bone. The bone plate 103 may have valves, as all of the embodiments are not intended to be limited in this manner.

Figure 3A:
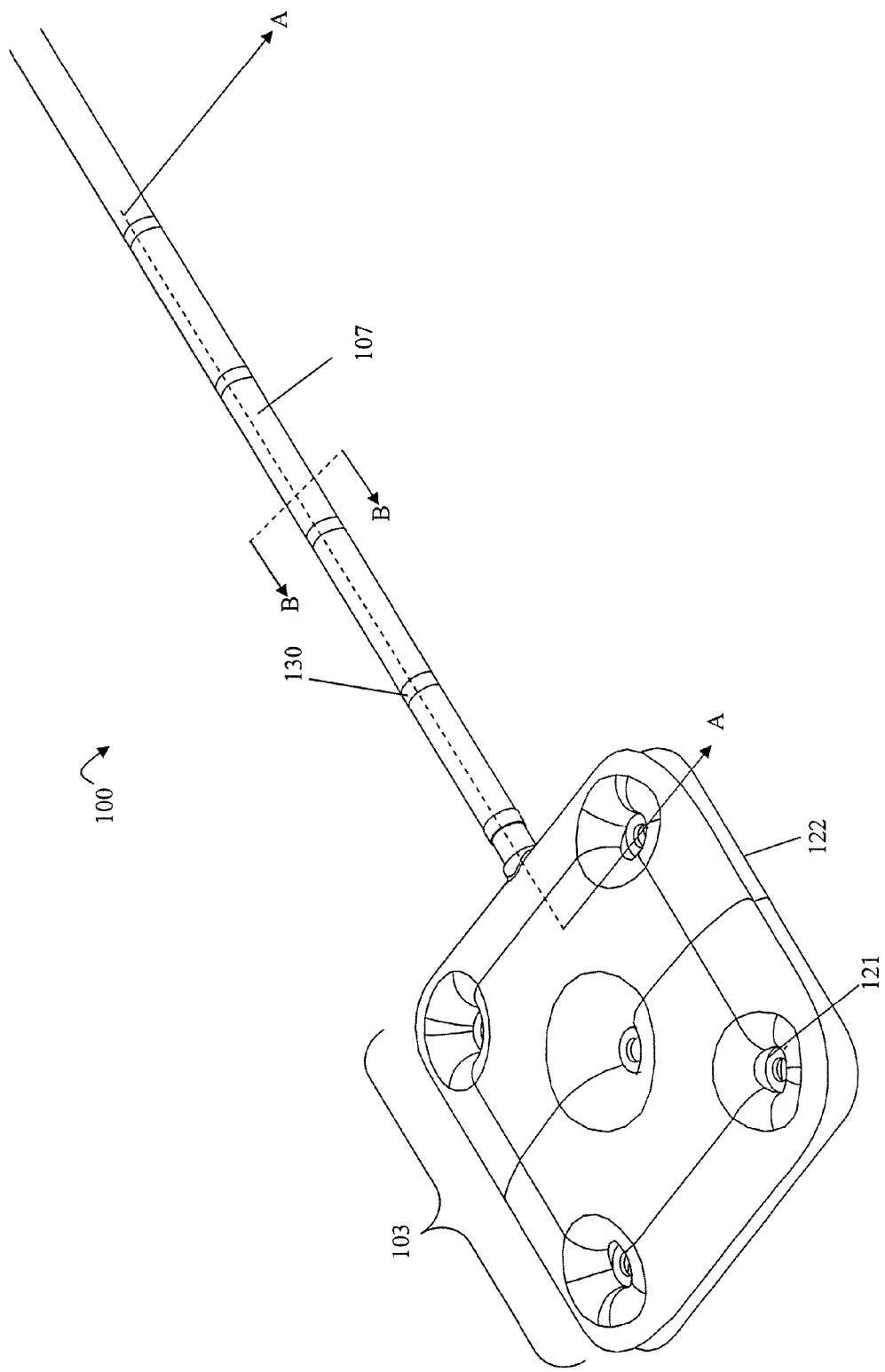
FIG. 3A, FIG. 3B and FIG. 3C show close-up views of some of the main components of a device for repairing a craniomaxillofacial injury of the presently disclosed embodiments.
Figure 3B:
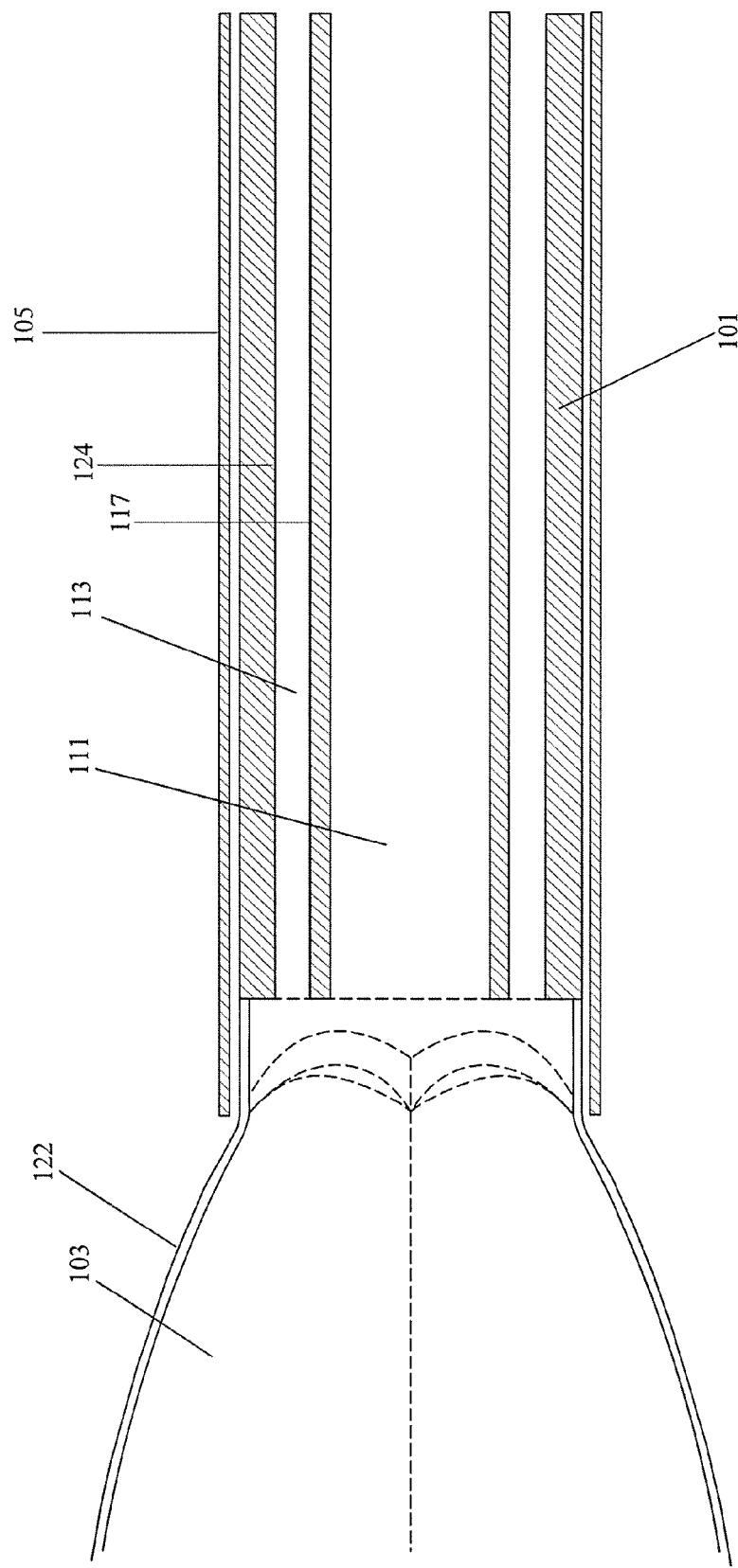
Figure 3C:
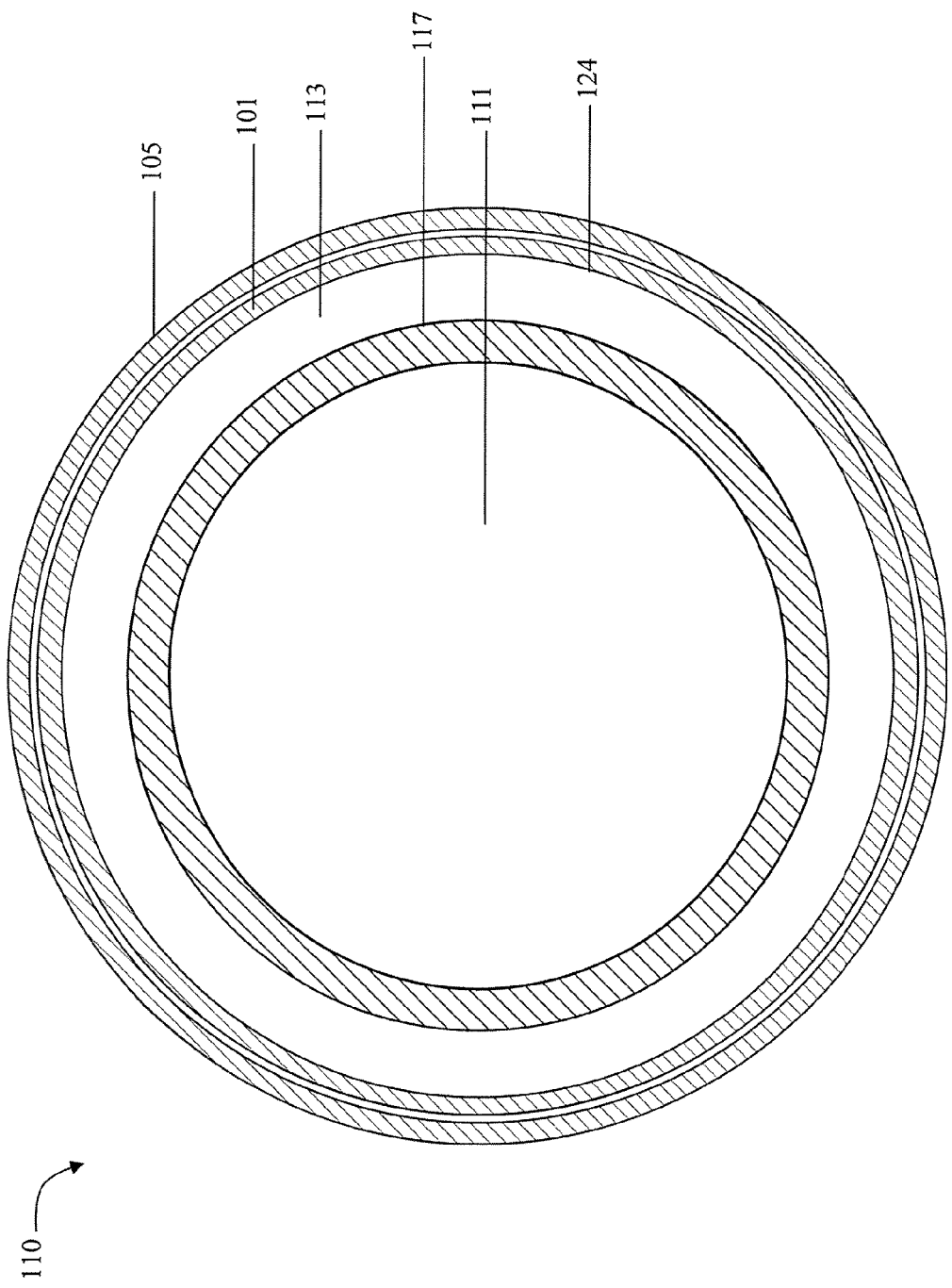

FIG. 3A, FIG. 3B and FIG. 3C show close-up views of some of the main components of the device 100. One or more radiopaque markers or bands 130 may be placed at various locations along the slip sleeve 107 of the device 100. Those skilled in the art will recognize that radiopaque markers 130 may also be placed at various locations along the bone plate 103. In an embodiment, the one or more radiopaque bands 130 are placed at intervals of about 10 mm along the length of the slip sleeve 107. The radiopaque markers 130 are formed using radiopaque material such as barium sulfate, tantalum, or other materials known to increase radiopacity. The radiopaque markers 130 provide visibility during inflation of the bone plate 103 to determine the precise positioning of the bone plate 103 and the delivery catheter during placement and inflation. The radiopaque markers 130 permit visualization of voids created by air that may be entrapped in the bone plate 103. The radiopaque markers 130 permit visualization to preclude the bone plate 103 from misengaging or not meeting the bony defects due to improper inflation.

Once the correct positioning of the bone plate 103 and delivery catheter are determined, the proximal end of the delivery catheter may be attached to a delivery system that contains a filling mixture.

FIG. 3B shows a cross-sectional view taken along line A-A of FIG. 3A. As shown in FIG. 3B, an elongated shaft 101 of the delivery catheter terminates in the bone plate 103 having the outer surface 122. Within the elongated shaft 101 of the delivery catheter 110 is a light pipe conduit 111 for accepting a light source (not shown). A void 113 for passage of at least one filling material is formed between an inner surface 124 of the delivery catheter and an outer surface 117 of the light pipe conduit 111. A delivery system comprising the at least one filling material may be attached to a side arm of a Tuohy-Borst adapter that is engaged to a proximal end of the delivery catheter. The at least one filling material passes through the void 113 of the delivery catheter and enters the bone plate 103. The infusion of the filling material causes the bone plate 103 to inflate to a desired state. In an embodiment, the filling material is infused through the void 113 in the delivery catheter to expand the bone plate 103 such that the bone plate 103 will resemble the contour of the new anatomy of an osteotomy, fracture or bone graft site. Orientation of the bones and bone plate 103 may be done without any visualization of the process or using x-ray or a fluoroscope. In an embodiment, a C arm imaging system is used as part of a fluoroscope. The C arm imaging system may allow movement or manipulation of the fluoroscope to rotate around tissue while viewing. Other techniques may be used for monitoring or inspecting the expansion of the bone plate 103 such as magnetic resonance imaging (MRI), ultrasound imaging, x-ray fluoroscopy, Fourier transform infrared spectroscopy, ultraviolet or visible spectroscopy. The bone plate 103 may be composed of non ferromagnetic materials and, thus, is compatible with MRI.

FIG. 3C shows a cross-sectional view taken along line B-B of FIG. 3A. In the embodiment shown in FIG. 3C, the outer slip sleeve has been removed. The stiffening member 105 surrounds and provides rigidity to the elongated shaft 101 of the delivery catheter 110. The light pipe conduit 111 provides a space for a light source to pass through. The void 113 is formed between the outer surface 117 of the light pipe conduit 111 and the inner surface 124 of the elongated shaft 101. This void 113 provides a passageway for the at least one filling material. The outer surface 117 of the light pipe conduit 111 allows for a separation between the light source and the filling material.

Figure 4:
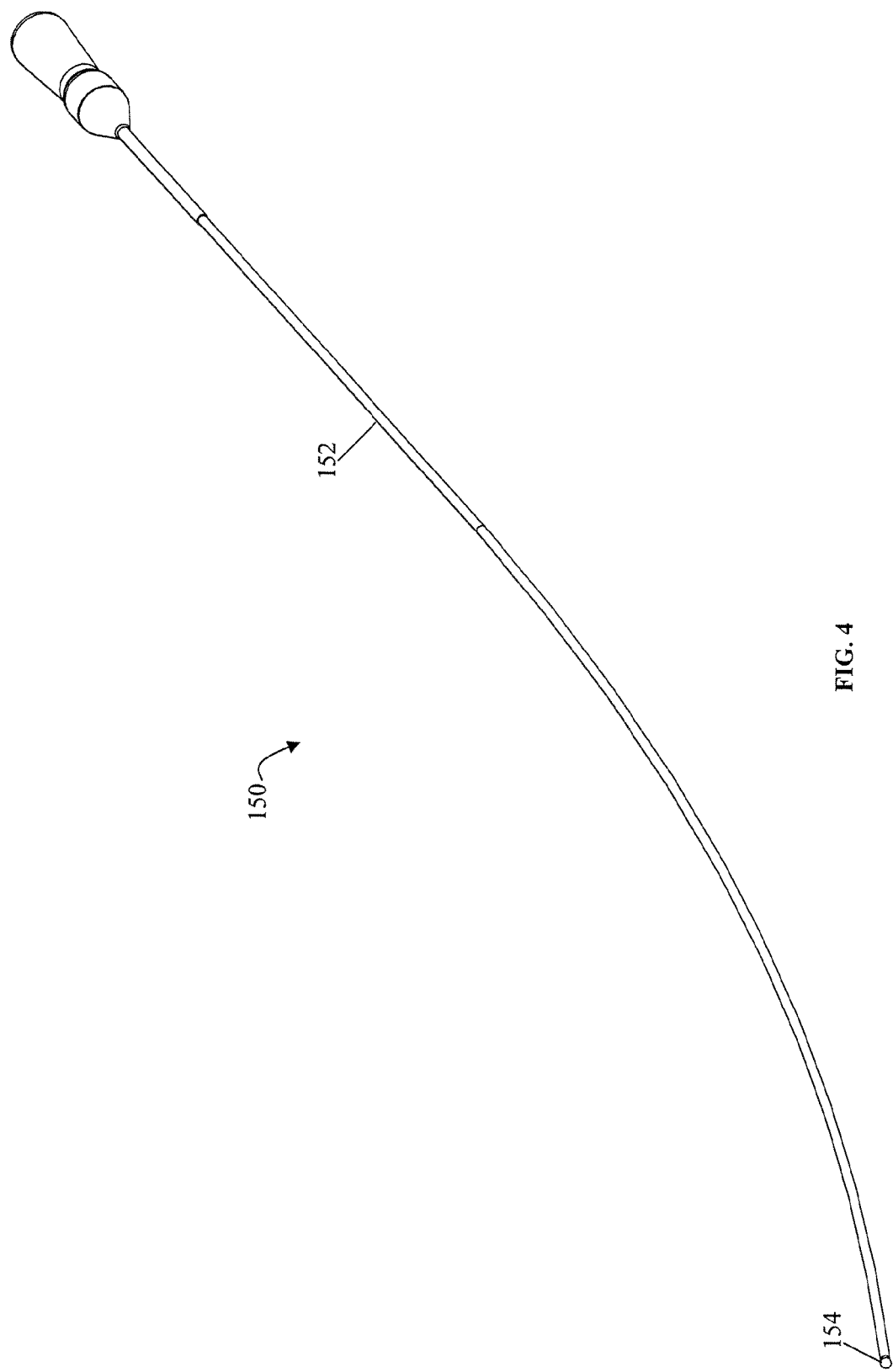
FIG. 4 shows a perspective view of a light source for use with a device for repairing a craniomaxillofacial injury of the presently disclosed embodiments.

FIG. 4 in conjunction with FIGS. 1A and 1B, shows a light source 150 for use with the device 100 of the presently disclosed embodiments. The light source 150 is used to harden the filling material that has been infused into the bone plate 103 through the delivery catheter 110. The light source 150 includes a light pipe 152 which terminates in an optical lens 154. Energy emitted from the light pipe 152 is projected through the optical lens 154 and guided into the bone plate 103 of the device 100. The optical lens 154 may be convex, concave or planar. The optical lens 154 is curved to converge or diverge the transmitted energy from the light pipe 152. In an embodiment, the optical lens 154 is made out of a plastic material such as Acrylic (PMMA), Polycarbonate (PC), Polystyrene (PS), or other similar materials known to those in the art such as Cyclic Olefin Copolymer (COC), and Amorphous Polyolefin (Zeonex). In an embodiment, the optical lens 154 is made out of a glass material such as quartz.

The light source 150 is introduced into a side arm of the adapter 115 that engages the proximal end 102 of the delivery catheter 110, as shown in FIG. 1A. The light source 150 runs through the elongated shaft 101 of the delivery catheter 110 through the light pipe conduit and up into the proximal end 123 of the bone plate 103A. The activation of the light source 150 cures the filling material resulting in the affixing of the bone plate 103 in an expanded shape. A cure may refer to any chemical, physical, and/or mechanical transformation that allows a composition to progress from a form (e.g., flowable form) that allows it to be delivered through the void in the delivery catheter 110, into a more permanent (e.g., cured) form for final use in vivo. For example, "curable" may refer to uncured composition, having the potential to be cured in vivo (as by catalysis or the application of a suitable energy source), as well as to a composition in the process of curing (e.g., a composition formed at the time of delivery by the concurrent mixing of a plurality of composition components).

In an embodiment, the filling material is a light cure adhesive or ultraviolet (UV) adhesive. A benefit of UV curing is that it is a cure-on-demand process and that adhesives may be free of solvents and include environmentally friendly resins that cure in seconds upon exposure to long wave UV light or visible light. Different UV adhesives use photoinitiators sensitive to different ranges of UV and visible light. Being very energetic, UV light can break chemical bonds, making molecules unusually reactive or ionizing them, in general changing their mutual behavior. Visible light, for example, visible blue light, allows materials to be cured between substrates that block UV light but transmits visible light (e.g., plastics). Visible light penetrates through the adhesive to a greater depth. Since the visible light penetrates through the adhesive, curing of the adhesive increases as a greater portion of the electromagnetic spectrum is available as useful energy. Additives may be used with the UV adhesive delivery system, including, but not limited to drugs (for example, antibiotics), proteins (for example, growth factors) or other natural or synthetic additives.

The electromagnetic spectrum is the range of all possible electromagnetic radiation. The electromagnetic spectrum of an object is the frequency range of electromagnetic radiation that the object emits, reflects, or transmits. The electromagnetic spectrum extends from just below the frequencies used for modern radio (at the long-wavelength end) to gamma radiation (at the short-wavelength end), covering wavelengths from thousands of kilometers down to fractions of the size of an atom. In an embodiment, the UV adhesive is a single-component, solvent-free adhesive that will not cure until a UV light engages the adhesive, and when that occurs, the adhesive will cure in seconds to form a complete bond with a shear strength. In an embodiment, the filling material exhibits a shrinkage upon cure of about 2 to about 3 percent.

UV light wavelength ranges from about 1 nm to about 380 nm, and can be subdivided into the following categories: near UV (380-200 nm wavelength; abbreviated NUV), far or vacuum UV (200-10 nm; abbreviated FUV or VUV), and extreme UV (1-31 nm; abbreviated EUV or XUV). Similarly, visible light has a wavelength spectrum of between about 380 to about 780 nm. Those skilled in the art will recognize that some UV adhesives may be activated by UV light, visible light, x-rays, gamma rays, microwaves, radio waves, long waves or any light having a wavelength less than about 1 nm, between about 1 nm and about 380 nm, between about 380 nm and about 780 nm, or greater than 780 nm, as not all embodiments are intended to be limited in that respect.

Using a UV light to cure the filling material assists in holding broken bones in place, filling of the bone plate, and viewing under a C arm imaging system. The filling materials cure in such a way that is sufficient to conform to the contour of a bony defect. More specifically, the ability to inflate, set, adjust, orient bones, and the resulting union of the bone are available prior to hardening the filling material. The introduction of the UV light starts the photoinitiator and the UV adhesive hardens. Once the UV light is introduced, the adhesive inside the bone plate hardens and the adhesives inside are affixed in place. Until the UV light is introduced, the bone placement is not disturbed or rushed as there is no hardening of the adhesives until the light is introduced, the bone plate may be inflated or deflated due to the viscosity of the adhesive. The adhesive may be infused or removed from the bone plate due to the low viscosity of the adhesive. In an embodiment, the viscosity of the filling material has a viscosity of about 1000 cP or less. In an embodiment, the filling material has a viscosity ranging from about 650 cP to about 450 cP. Not all embodiments are intended to be limited in this respect and some embodiments may include filling materials having a viscosity exactly equal to or greater than 1000 cP. In an embodiment, a contrast material may be added to the filling material without significantly increasing the viscosity. Contrast materials include, but are not limited to, barium sulfate, tantalum, or other contrast materials known in the art.

Several epoxies known in the art are suitable for use as filling materials and vary in viscosity, cure times, and hardness (durometer or shore) when fully cured. A durometer of a material indicates the hardness of the material, defined as the material's resistance to permanent indentation. Depending on the amount of resultant support that is necessary for a given bony defect, a specific durometer UV adhesive may be chosen. Alternately, multiple UV adhesives having varying durometers may be chosen for the repair of a bony defect and be within the scope and spirit of the presently disclosed embodiments. The durometer of a material may be altered to achieve either greater rigidity or a more malleable result. The mechanical properties of the epoxies may dictate using methods/measures that are typical for high-strength and high-impact materials including but not limited to, tensile strength and tensile modulus, tensile strength tests, ultimate modulus, Poisson's ratio, hardness measurements like Vickers and Charpy Impact which measures yield strength and toughness.

In an embodiment, the filling material is cured by chemical activation or thermal activation. Chemical activation includes but is not limited to water or other liquids. In an embodiment, the filling material is a drying adhesive which has a polymer dissolved in a solvent such that as the solvent evaporates, the adhesive hardens. In an embodiment, the filling material is a hot or thermoplastic adhesive such that as the adhesive cools, the adhesive hardens.

Some filling materials may require or be enhanced by curing via any means, such as UV or visible light, heat, and/or addition or removal of a chemical or substance, may utilize any outside or internal processes to cure the material, or may not require curing.

In an embodiment, carbon nanotubes (CNTs) are added to the filling material to increase the strength of the material.

Carbon nanotubes are an allotrope of carbon that take the form of cylindrical carbon molecules and have novel strength properties. Carbon nanotubes exhibit extraordinary strength. Nanotubes are members of the fullerene structural family, which also includes buckyballs. Whereas buckyballs are spherical in shape, a nanotube is cylindrical with at least one end typically capped with a hemisphere of the buckyball structure. Nanotubes are composed entirely of sp2 bonds, similar to those of graphite. This bonding structure, which is stronger than the sp3 bonds found in diamond, provides the molecules with their unique strength. Nanotubes naturally align themselves into "ropes" held together by Van der Waals forces. Single walled nanotubes or multi-walled nanotubes may be used to strengthen the filling materials.

In an embodiment, a central space may remain in the bone plate 103 which may be filled in order to provide extra strength and support to the fractured bones. An optical rod or similar device may be positioned in the central space and turned on or illuminated. An optical rod or similar device can be made of fiber, silica, quartz, sapphire or similar materials. The end of the optical rod may be cut and remain in the bone plate 103 to provide increased rigidity.

Figure 5A:
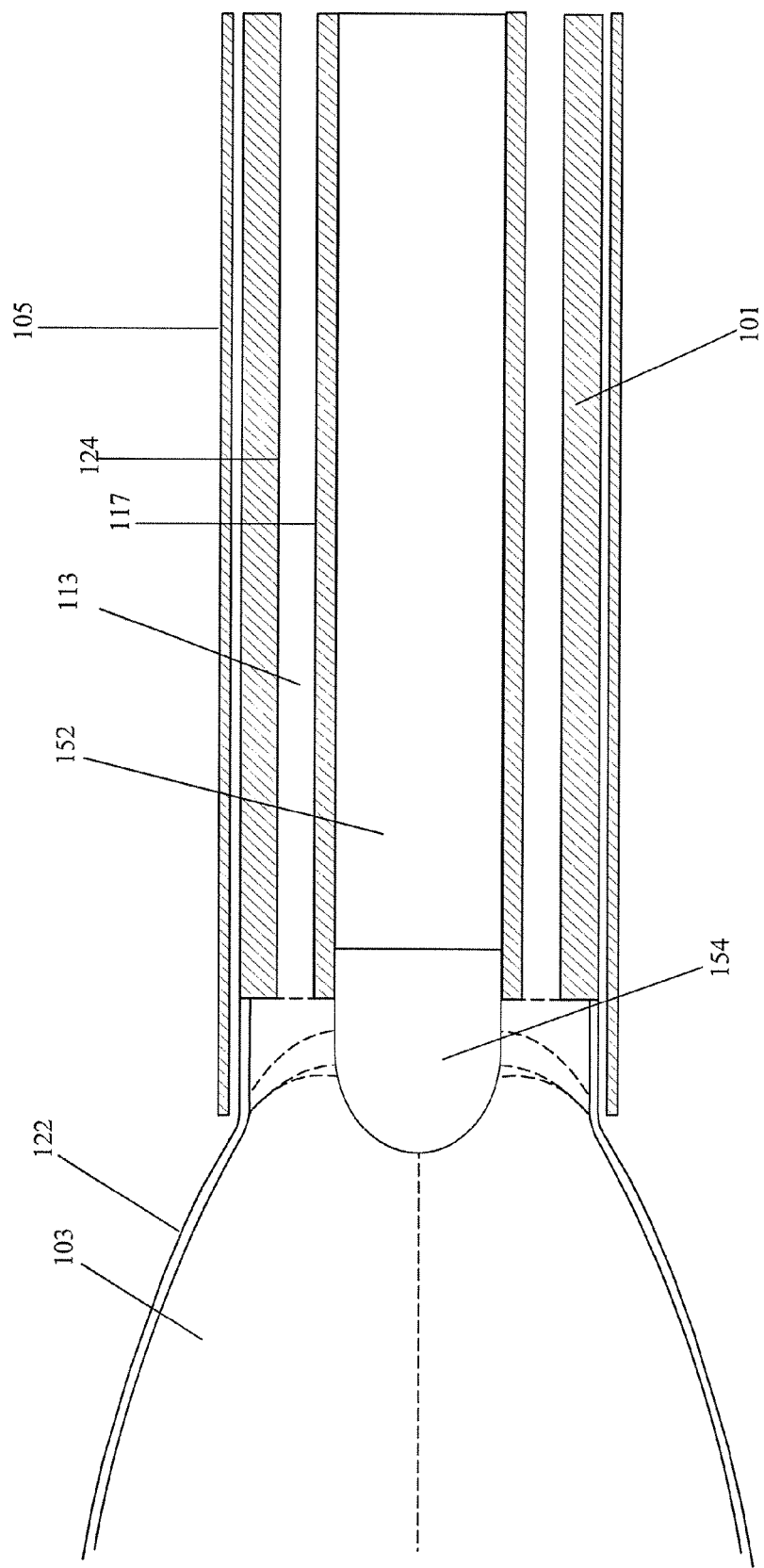
FIG. 5A and FIG. 5B show close-up cross-sectional views of some of the main components, including a light pipe, of the device for repairing a craniomaxillofacial injury of the presently disclosed embodiments.
Figure 5B:
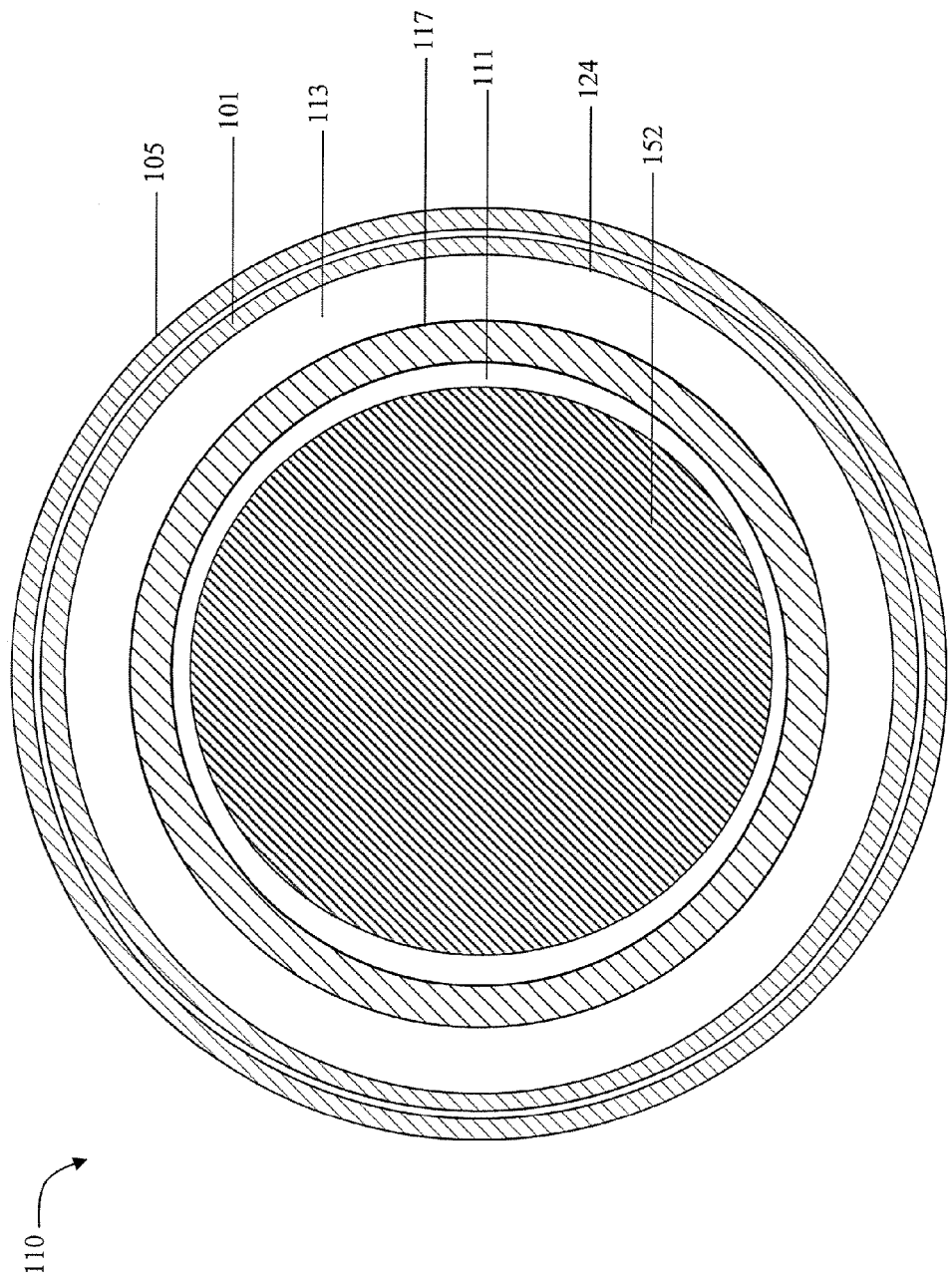

FIG. 5A and FIG. 5B show cross-sectional views of the device 100 of FIG. 1A, showing the light source 150 of FIG. 4 passing through the light pipe conduit 111 of the delivery catheter 110, through the opening 147 and into the inner space of the pad along the longitudinal axis of the pad. The light source includes the light pipe 152 terminating in the optical lens 154. The light source is used to harden the filling material that has been infused into the bone plate 103 of the device 100. Energy from the light source 150 is emitted from the light pipe 152, projected through the optical lens 154, and guided into the bone plate 103 of the device 100. The optical lens 154 may be convex, concave or planar. The optical lens 154 is curved to converge or diverge the transmitted energy from the light pipe 152.

Millions of people sustain trauma to the head and face resulting in complex fractures which, if not correctly diagnosed and treated, may cause permanent functional and cosmetic deformities. In acute trauma cases, the goal of reconstruction is a one-stage repair which has been made possible by the application of craniofacial techniques. Delayed treatment has been replaced by early or immediate surgical treatment and stabilization of small bone fragments augmented by bone grafts and miniplate fixation. These recent advances have allowed surgeons to approach and often reach the goal of restoring preinjury facial appearance and function while at the same time minimizing revisional surgery. Without treatment in a timely manner, many individuals will develop future problems, the severity and consequences of which can be much greater than if the injury had been immediately repaired. Craniofacial surgery encompasses the reconstruction of a broad spectrum of facial deformities including, but not limited to, zygomatic fractures, maxillary fractures, naso-ethmoid orbital fractures, internal orbital fractures, mandibular fractures, post-traumatic facial deformities, soft tissue deformities, and facial bone contouring. An implant for fracture fixation must be strong, ductile, adaptable to the bone surface and biocompatible. Fixation system quality includes adequate strength and rigidity, avoiding adverse reactions, interference with bone healing, intracranial migration, visibility and palpability and implant removal operation.

FIG. 6 illustrates the device 100 of the presently disclosed embodiments in use during a procedure for repairing a craniomaxillofacial bony defect in a patient. The procedure begins with placing the deflated bone plate 103 of the device 100 at the bony defect, where the bone plate 103 spans at least two bone fragments (A and B in FIG. 6). A delivery system, such as the syringe 160 filled with the filling material (not shown), is attached to the device 100. The filling material is then infused through the inner void in the elongated shaft of the delivery catheter 110 and enters the bone plate 103 of the device 100, causing the bone plate 103 to move from a deflated state to an expanded state. Once the bone plate 103 has been expanded to a desired level (which is controlled by a medical professional with the syringe 160), and orientation of the bone fragments are confirmed to be in a desired position, the light source 152 is attached to the device 100. The light source 152 is passed through the elongated shaft of the delivery catheter 110 through the light pipe conduit. In an embodiment, the filling material is a UV curable glue which requires a UV light source to cure the adhesive. The light source 152 is then activated which causes the filling material to harden. The hardened bone plate 103 may be affixed to the bony defect site, thus stabilizing the fracture. The light source 152 is removed from the device 100 and the bone plate 103 is released from the delivery catheter 110. In an embodiment, the delivery catheter 110 is cut to separate the bone plate 103 from the elongated shaft 101. A device slides over the delivery catheter 110 and allows a right angle scissor to descend through the delivery catheter 110 and make a cut. The location of the cut may be determined by using a fluoroscope or an x-ray. In an embodiment, the cut location is at the junction where the elongated shaft 101 meets the bone plate 103.

In an embodiment, a separation area is located at the junction between the proximal end 123 of the bone plate 103 and the delivery catheter 110. The separation area may also include an illumination band. When activated, the illumination band causes light to cure the filling material located in the bone plate 103 within the illumination band. The illumination band extends around the delivery catheter 110 and has a stress concentrator. The stress concentrator may be a notch, groove, channel or similar structure that concentrates stress in the illumination band. The stress concentrator of the illumination band may be notched, scored, indented, pre-weakened or pre-stressed to direct separation of the bone plate 103 from the elongated shaft of the delivery catheter 110 under specific torsional load. The separation area ensures that there are no leaks of filling material from the elongated shaft of the delivery catheter 110 and/or the bone plate 103. The separation area seals the bone plate 103 and removes the elongated shaft of the delivery catheter 110 by making a break at a known or predetermined site (e.g., a separation area). The separation area may be various lengths and up to about an inch long. When torque (twisting) is applied to the delivery catheter 110, the elongated shaft separates from the bone plate 103. The twisting creates a sufficient shear to break the residual filling material and create a clean separation of the plate/shaft interface. The illumination band may be connected to the light source and may be activated by a separate switch. Having a distinct switch to activate the illumination band may help to prevent inadvertent delivery of light from the light source to cure the filling material. The activation of the illumination band seals the bone plate 103 and seals the end of the delivery catheter 110, and ensures that there is a "hard seal" of the filling material at the illumination band allowing no filling material to leak from the bone plate 103 or the delivery catheter 110.

The bone plate 103 may be fastened to the bony defect before, after or during a repair procedure. Fasteners 163 are disposed through the apertures 121 and engage the bone plate 103 to secure the bone plate 103 to one or more portions of bone.

A method for adjoining at least two bone fragments includes providing a device for adjoining at least two bone fragments, the device including a conformable bone plate engaged to a delivery catheter having an elongated shaft with a proximal end, a distal end, and a longitudinal axis therebetween, wherein the conformable bone plate has at least one aperture extending from a first surface of the bone plate to a second surface of the bone plate for receiving a fastener to affix the bone plate to the at least two bone fragments; positioning the conformable bone plate over an exterior surface spanning the at least two bone fragments; attaching a delivery system housing at least one filling material to the delivery catheter, wherein the elongated shaft of the delivery catheter has an inner void for passage of the at least one filling material to the conformable bone plate; inserting a light source into the delivery catheter, wherein the elongated shaft of the delivery catheter has an inner lumen for passage of the light source to the conformable bone plate; infusing the at least one filling material through the elongated shaft of the delivery catheter and into the conformable bone plate to expand the conformable bone plate; activating the light source to harden the at least one filling material in the expanded conformable bone plate; releasing the hardened conformable bone plate from the delivery catheter; and affixing the conformable bone plate to the exterior surfaces of the at least two bone fragments to adjoin the bone fragments. In an embodiment, the at least two bone fragments are bones of the face. In an embodiment, the light source is removed from the delivery catheter once the at least one filling material has been hardened.

The bone plates and devices disclosed herein have been discussed in the repair of a craniomaxillofacial bony defect. Those skilled in the art will recognize that the bone plates and devices may be used in a variety of areas, such as bones of the vertebrae and any other fractured bone that required support on its exterior surface so as to hold the disassociated portions in alignment during healing.

All patents, patent applications, and published references cited herein are hereby incorporated by reference in their entirety. It will be appreciated that various of the above-disclosed and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

What is claimed is:

1. A device for adjoining at least two bone fragments comprising:
   a delivery catheter having an elongated shaft with a proximal end, a distal end, and a longitudinal axis therebetween;
   a flexible expandable conformable bone pad releasably engaging to the distal end of the delivery catheter,
   the flexible expandable conformable bone pad includes a first bone contacting surface and an opposing second outer surface, a left side surface and an opposing right side surface extending between the first bone contacting surface and the second outer surface, and a proximal surface and an opposing distal surface extending between the first bone contacting surface and the second outer surface defining an inner space in communication with an inner void of the delivery catheter for passage of at least one filling material into the inner space for expanding the flexible expandable conformable bone pad and in communication with an inner lumen of the delivery catheter for passage of an optical fiber into the inner space to transmit light from a light source into the inner space for hardening the at least one filling material in the inner space of the conformable bone pad such that the flexible expandable conformable bone pad is contoured to engage against the at least two bone fragments;
   an opening at the proximal surface of the conformable bone pad to pass the at least one filling material and the optical fiber into the inner space of the conformable bone pad;
   a major longitudinal axis running from the proximal surface to the distal surface;
   a minor longitudinal axis running from the first bone contacting surface to the second outer surface and intersecting the major longitudinal axis at an intersection;
   at least one centered through aperture extending from the second outer surface to the first bone contacting surface through a center of the conformable bone pad and through the intersection of the minor longitudinal axis and the major longitudinal axis of the conformable bone pad for receiving a fastener through the conformable bone pad; and
   one or more peripheral through apertures extending from the second outer surface to the first bone contacting surface at the periphery of the conformable bone pad for receiving a fastener through the conformable bone pad.

2. The device of claim 1 wherein the adjoining of the at least two bone fragments occurs at an exterior surface of the bone fragments.

3. The device of claim 1 wherein the at least two bone fragments are craniomaxillofacial bones.

4. The device of claim 1 wherein at least one surface of the bone pad is textured.

5. The device of claim 1 wherein the conformable bone pad is constructed from a polymer material.

6. The device of claim 1 wherein the at least one filling material is a light curable glue.

7. The device of claim 1 the light source emits visible light for curing the at least one filling material.

8. The device of claim 1 wherein the optical fiber guides visible light from the light source into the conformable bone pad to harden the at least one filling material.

9. The device of claim 1 wherein the optical fiber passes into the inner space through the opening along the major longitudinal axis of the conformable bone pad.

10. The device of claim 1 wherein a fastener is received through the centered through aperture for securing the conformable bone plate to the bone fragments.

* * * * *